United States Patent
Wang et al.

(10) Patent No.: US 10,472,654 B2
(45) Date of Patent: Nov. 12, 2019

(54) POLYMER GRADE LACTIC ACID MONOMER PRODUCTION BACTERIA AND CONSTRUCTION METHOD THEREOF AND TECHNOLOGY FOR MANUFACTURING LACTIC ACID

(71) Applicant: Tianjin University of Science and Technology, Tianjin (CN)

(72) Inventors: Zhengxiang Wang, Tianjin (CN); Kangming Tian, Tianjin (CN); Dandan Niu, Tianjin (CN); Fuping Lu, Tianjin (CN)

(73) Assignee: Tianjin University of Science and Technology, Tianjin (CN)

( * ) Notice: Subject to any disclaimer, the term of this patent is extended or adjusted under 35 U.S.C. 154(b) by 0 days.

(21) Appl. No.: 15/818,724

(22) Filed: Nov. 20, 2017

(65) Prior Publication Data
US 2018/0073045 A1 Mar. 15, 2018

Related U.S. Application Data

(63) Continuation of application No. PCT/CN2015/093686, filed on Nov. 3, 2015.

(30) Foreign Application Priority Data

May 21, 2015 (CN) .................. 2015 1 02627695

(51) Int. Cl.
*C12N 1/21* (2006.01)
*C12P 7/56* (2006.01)
*C12R 1/19* (2006.01)

(52) U.S. Cl.
CPC . *C12P 7/56* (2013.01); *C12R 1/19* (2013.01)

(58) Field of Classification Search
CPC ........................................... C12P 7/56
See application file for complete search history.

(56) References Cited

PUBLICATIONS

L. Zhou et al. "Evaluation of Genetic Manipulation Strategies on D-Lactate Production by *Escherichia coli*", Current Microbiology 62: 981-989 (Year: 2011).*
D. Niu et al. "Highly efficient L-lactate production using engineered *Escherichia coli* with dissimilar temperature optima for L-lactate formation and cell growth", Microbial Cell Factories 13:78 (Year: 2014).*
S. Mazumdar et al. "Efficient synthesis of L-lactic acid from glycerol by metabolically engineered *Escherichia coli*", Microbial Cell Factories 12:7 (Year: 2013).*

* cited by examiner

*Primary Examiner* — Rebecca E Prouty
(74) *Attorney, Agent, or Firm* — Tony C. Hom, Esq.

(57) ABSTRACT

Disclosed are very high optically pure D- and L-lactic acid fermentation production strains and construction methods thereof and the method for preparing very high optically pure D- and L-lactic acids using the strains, wherein the deposit number of the D-lactic acid fermentation production strain is CGMCC No. 11059, and the deposit number of the L-lactic acid fermentation production strain is CGMCC No. 11060.

1 Claim, 12 Drawing Sheets

POLYMER GRADE LACTIC ACID MONOMER PRODUCTION BACTERIA AND CONSTRUCTION METHOD THEREOF AND TECHNOLOGY FOR MANUFACTURING LACTIC ACID

RELATED APPLICATIONS

This application is a continuation of International Application PCT/CN2015/093686, filed Nov. 3, 2015, which claims the priority of Chinese Patent No. 201510262769.5 filed on May 21, 2015 and entitled "Strain for Constructing Lactic acid as well as Preparation Method and Application Thereof" the disclosure of which is hereby incorporated by reference herein in its entirety.

TECHNICAL FIELD

The present disclosure relates to the field of microbial application, especially relates to a polymer grade lactic acid monomer production bacteria and construction method thereof and technology for manufacturing lactic acid.

BACKGROUND

Biodegradable materials are kinds of new materials capable of being degraded and used by environmental organisms (microorganisms). A new generation of biodegradable materials takes polylactic acid as representative, the polylactic acid is divided into poly-L-lactic acid and poly-D-lactic acid, which are obtained by the polymerization of L-lactic acid monomer or D-lactic acid monomer, respectively. It is estimated that the global demand for polylactic acid will reach 15 million tons per year by 2020, and the polylactic acid will be the most likely substitute of Polyethylene terephthalate (PET) and Polystyrene (PS) which have an annual demand of 50 million tons.

The poly D-lactic acid material polymerized by high-quality D-lactic acid as raw material can be a good alternative to fiber, plastic and other products polymerized by common chemical product. Especially in the field of high-end consumer products, such as in the processing and polymerization of diapers built-in gaskets, cigarette filter heads and other materials, a unique biomass material characteristic, biological compatibility and non-toxic and harmless characteristics of it could greatly improve the quality of related products, and the market space is huge. A new product prepared by 3D printing technology using the poly-D-lactic acid as raw material has environmental protection, good mechanical property, safety and other multiple advantages, so it is widely used in cars, disposable supplies, electronics, medical and other fields. More worth noting is that the blending of the high-quality polylactic acid (PLA) polymerized by the extremely high optical pure D-lactic acid and L-lactic acid with the biodegradable butylene succinate-butylene adipate copolymer (PBSA) can greatly improve the strength and toughness of biodegradable material, and expand the application field of related products. At present, trial production of blending products of PLA and PBSA has been completed by companies such as BASF and the like, a series of new biodegradable materials with excellent performances were successfully launched, and the relevant development greatly increased the market requirements of the extremely high optical pure D-lactic acid and L-lactic acid.

Due to its own characteristics and the complexity of the medium required, the optical purity of lactic acid produced by traditional lactic acid producing strain such as *Rhizopus Oryzae* and *Lactobacillus Acidophilus* is unable to meet the requirement of polymer grade and cannot be used for scale production of extremely high optical pure D-lactic acid and L-lactic acid. Recombinant yeast and recombinant *Escherichia coli* are able to produce extremely high optical pure D-lactic acid and L-lactic acid, and also have the advantages of low nutritional requirements, being easy to be cultured with a high density and popularized in industrial-scale, which made the recombinant yeast and recombinant *Escherichia coli* became hot research of producing strains of extremely high optical pure D-lactic acid and L-lactic. Compared with the recombinant yeast, multiple genetically modified *E. coli* is able to produce extremely high optical pure and extremely high chemical pure lactic acid. Due to the culture temperature of the *E. coli* is obviously higher than that of the yeast, the fermentation period of *E. coli* for lactic acid production is greatly shortened compared with recombinant yeast. Therefore, the recombinant *E. coli* is considered to be the most ideal strain for producing extremely high optical pure D-lactic acid and L-lactic acid in industrial scale.

Especially in recent years, *E. coli* has been widely recognized as a D-lactic acid producing strain. If *E. coli* can also be used for production of high-optical-purity L-lactic acid, it will be important significance for alternate production of D-lactic acid and L-lactic acid on the same production line. In addition, the rapid development of high-quality lactic acid monomer and the polylactic acid manufacturing industry is also facilitated.

A number of well-studied researches about the production of extremely high optical pure D-lactic acid by recombinant *E. coli* as a producing strain have been carried out (Zhou L. et al, Current Microbiology, 2011, 62: 981-989; Zhu Y. et al., Applied Environmental Microbiology, 2007, 73: 456-464; Zhou S. et al., Applied Environmental Microbiology, 2003, 69: 399-407; Zhu J. et al., Applied Microbiology and Biotechnology, 2004, 64: 367-375, Zhu J. et al., Metabolic Engineering, 2005, 7:104-115; Bunch P. K. et al., Microbiology, 1997, 143: 187-195). For example, 1) Strict anaerobic fermentation to improve acid production efficiency (Li et al., Applied Microbiology and Biotechnology, 2002, 60: 101-106); 2) Low-stirring limited oxygen fermentation under stopping ventilation condition to improve acid production efficiency (Zhou L. et al., Current Microbiology, 2011, 62:981-989); 3) Maintaining micro-aerobic fermentation conditions to increase acid production efficiency (Tian K et al., 2012 African Journal of Biotechnology, 11(21): 4860-4867; Zhou L et al., Biotechnology letters 2012, 34:1123-1130); 4) Adopting suitable culture temperature for cell growth and sub-suitable growth temperature limiting the cell growth to increase fermentation and acid production efficiency (Niu D et al., Microbial Cell Factories 2014, 13:78-88; Zhou L et al., Metabolic Engineering, 2012, 14:560-568); 5) Using different carbon sources in the cell growth and fermentation of acid to improve the acid production efficiency and other method (Zhu L et al., Applied Environmental Microbiology, 2007, 73: 456-464).

The inventor's patent issued earlier (Chinese Patent, Patent Number: ZL201210102731.8) disclosed that introducing a temperature regulation element in the gene transcription level, and the synthesis efficiency of the D-lactic acid is greatly improved by matching with the fermentation temperature regulation and control strategy. Based on this, the present disclosure introduced a regulatory mechanism of cell growth quantity control, and a double-switch mechanism of a cell growth process and a D-lactic acid synthesis process is formed, resulting in further improvement of the D-lactic acid synthesis efficiency.

SUMMARY OF THE INVENTION

The technical problem to be solved by the present disclosure is to provide polymer grade lactic acid monomer producing strains.

Another technical problem to be solved by the present disclosure is to provide a construction method of the polymer grade lactic acid monomer producing strains.

Another technical problem to be solved by the present disclosure is to provide a method for manufacturing lactic acid using the polymer grade lactic acid monomer producing strain, specifically, a high efficiency, low-cost and easy to implement microbiological method producing extremely high optical pure lactic acid monomer which is formed by combining characteristics of strain metabolism, growth and acid producing processes and industrial scale production.

In order to solve the technical problems above, the technical schemes of the invention are as follows:

A polymer grade lactic acid monomer producing strain for producing extremely high optical pure D-lactic acid by fermentation, the deposit number of the strain is CGMCC No. 11059 (equals to the strain with number B0013-090B in the examples).

A polymer grade lactic acid monomer producing strain for producing extremely high optical pure L-lactic acid by fermentation, the deposit number of the strain is CGMCC No. 11060 (equals to the strain with number B0013-101J in the examples).

The polymer grade lactic acid monomer producing strain used to produce extremely high optical pure D-lactic acid and the polymer grade lactic acid monomer producing strain used to produce extremely high optical pure L-lactic acid are capable of producing extremely high optical pure D-lactic acid and L-lactic acid respectively, the optical purity can be higher than 99.9%, the optical purity of D-lactic acid and L-lactic acid all can meet the requirement to the lactic acid monomer in the high-quality polylactic acid polymerization process.

The polymer grade lactic acid monomer producing strain used to produce extremely high optical pure D-lactic acid and the polymer grade lactic acid monomer producing strain used to produce extremely high optical pure L-lactic acid are capable of producing extremely high chemical pure D-lactic acid and L-lactic acid respectively, the chemical purity can be higher than 99.9%, after a simple subsequent treatment and even no treatment, the chemical purity of D-lactic acid and L-lactic acid can meet the requirement to the lactic acid monomer in the high-quality polylactic acid polymerization process.

A construction method of the polymer grade lactic acid monomer producing strain used to produce extremely high optical pure D-lactic acid and the polymer grade lactic acid monomer producing strain used to produce extremely high optical pure L-lactic acid above mentioned is:

knocking out a single or a plurality of genes for preliminary strain construction, the genes include: ldhA, thiE, dld, ackA, pta, pps, pflB, poxB, frdA, adhE, lldD; expressing the single or a plurality of genes, the genes include: kan-clts857-$p_R$-$p_L$ldhA, ldhBcoa, ldhLca, ldhStrb;

using a temperature-induced gene transcription mode to control and regulate the cell growth process and the lactic acid formation process, including: after being preliminarily constructed, the strain is subjected to cell fermentation culture-induction-acid production stage-by-stage under the condition of 25-50° C., quantitative control of the cell accumulation can be performed in the cell growth process under the regulation of a single fermentation factor, wherein the said single fermentation factor is a regulation factor in the transcriptional process, the translation process, the secretion process or the catalytic process after expression of a key enzyme of a cell central metabolic pathway.

Preferably, in the construction method of the polymer grade lactic acid monomer producing strain above mentioned, the quantitative control of the cell accumulation can be calculated in advance, then controlled accurately by adding a certain amount of single fermentation factor in different fermentation systems according to actual requirements of production process.

Preferably, in the construction method of the polymer grade lactic acid monomer producing strain above mentioned, the growth processes of the strain after being preliminarily constructed are associated with regulation and control of the single fermentation factor, wherein the single fermentation factor can be a carbon source, such as glucose, glycerol; can also be a nitrogen source, such as yeast extract, peptone, ammonium sulfate, ammonium hydrogen phosphate; can also be metal ions, such as iron ions, magnesium ions, calcium ions, zinc ions, manganese ions, cobalt ions, copper ions, sodium ions and potassium ions, and can also be nutrient elements, such as VB1, VB6, VB12, biotin, thiamine chloride, thiamine pyrophosphate and the like, particularly, one single fermentation factor can quantitatively control the accumulation process of cells, and make sure the cells can be rapidly accumulated and possess high activity; and the synthesis process of lactic acid can be started or stopped in a switch-controlled manner, and the regulation and control process can be completed by adding corresponding fermentation factors in advance in the process.

A method for manufacturing lactic acid, specifically comprises the following steps; using the polymer grade lactic acid monomer producing strain above mentioned; conducting the growth process of host cells of the strain rapidly in an total-synthetic inorganic salt medium, wherein the total synthesis inorganic salt culture medium is a thiamine-containing medium, the host cell grow fast in the total-synthetic inorganic salt medium, wherein, in a 7L fermentation system the biomass is accumulated to 11.5 g/L of the dry weight of cells in 8-10 h, and the dry weight of cells is subjected to higher accumulation by adding a single fermentation factor, and no large amount of lactic acid is formed in the host cell culture process, namely the trace amount of lactic acid does not affect the growth of cells; the host cells accumulate lactic acid quickly after the growth is completed.

Preferably, in the method for manufacturing lactic acid above mentioned, the D-lactic acid accumulation process can be switched to the L-lactic acid accumulation process in the same production system by replacing corresponding polymer grade lactic acid monomer production bacteria, vice versa.

The addition of organic matters in the total-synthetic inorganic salt medium does not influence the process of high-density culture of the cells, but the high-density culture process of the cell is facilitated without organic matters.

Preferably, in the method for manufacturing lactic acid above mentioned, main components of the total-synthetic inorganic salt medium are as follows:

A fermentation medium for D-lactic acid production (g/L): diammonium hydrogen phosphate 0-25, monopotassium phosphate 0-5, disodium hydrogen phosphate 0-25, sodium chloride 0-5, $MgSO_4$ 0-0.5, $FeSO_4$ 0-1, $FeCl_3$ 0-1, $CoCl_2$ 0-1, $CuCl_2$ 0-1, $Na_2MoO_4$ 0-1, $H_3BO_3$ 0-1, $MnCl_2$ 0-1, citric acid 0-25, thiamine 0-1, xylose 0-50, glycerol 0-50, glucose 0-50, sulfuric acid 0-5, pH 6.0-7.5.

A fermentation medium for L-lactic acid production (g/L): diammonium hydrogen phosphate 0-25, monopotassium phosphate 0-5, disodium hydrogen phosphate 0-25, sodium chloride 0-5, $MgSO_4$ 0-0.5, $FeSO_4$ 0-1, $FeCl_3$ 0-1, $CoCl_2$ 0-1, $CuCl_2$ 0-1, $ZnCl_2$ 0-1, $Na_2MoO_4$ 0-1, $H_3BO_3$ 0-1, $MnCl_2$ 0-1, citric acid 0-25, thiamine 0-1, xylose 0-50, glycerol 0-50, glucose 0-50, sulfuric acid 0-5, pH 6.0-7.5.

The acid production fermentation process has a characteristic of settable automatic starting, the acid production process is automatically started by the change of the content of the corresponding regulation factor components in the medium when the cells grow to a specific stage by combining the medium components and growth characteristics of the strain.

Preferably, in the method for manufacturing lactic acid above mentioned, the growth process of the strain and the lactic acid formation process are all associated with the fermentation temperature, the acid production process is completed at non-constant temperatures; the change of the fermentation temperature shows a gradient-rising trend according to the acid production characteristic of the producing strain; and there is a certain combination mode, under which the influence of the temperature on the acid production process is most significant, and the acid production efficiency is the highest, for example: the rising of fermentation temperature slows down the growth, the reduction of fermentation temperature accelerates the growth very rapidly, which is suitable for accumulating high-activity cells; the lactic acid can be rapidly formed when the fermentation temperature is risen, and the lactic acid can be slowly or even not formed when the fermentation temperature is lowered, which is suitable for high-efficiency accumulation of lactic acid.

Preferably, in the method for manufacturing lactic acid above mentioned, the strain grows rapidly at 25-36° C. with glucose to form thallus, and then rapidly accumulates lactic acid with glucose at 37-50° C.

The transcription of genes ldhA and BcoaLDH encoding a key enzyme for the synthesis of D-lactic acid and L-lactic acid, is strongly inhibited when the strain is at lower temperatures, such as 25-36° C., whereas at higher temperatures, such as 37-50° C., the transcription of ldhA and LDHBcoa is strongly started, we can see that, the growth temperature of the strain and the lactic acid formation temperature may be a continuous process at a single temperature, and can also be a gradient combination process of a plurality of temperature points. More preferably, the gradient combination process of a plurality of temperature points is used.

Preferably, the method for manufacturing lactic acid above mentioned, specifically comprises the following steps:

(1) dynamically regulating the expression of lactate dehydrogenase encoding gene on the chromosomes of D-lactate and L-lactate high-yield recombinant strains under simple conditions through genetic engineering to obtain acid producing strains;

(2) aerobically culturing the strains at 25-36° C., 200 r/min for 6-10 h, then staying at 37-45° C. for the lactic acid fermentation, and then analyzing the cell density, sugar consumption, lactic acid yield, main metabolic intermediates, other organic acid products and the like using the starting strain B0013-070 as a control to determine the induction time of lactic acid synthesis; wherein the strains are subjected to shake flask culture with 0.06-100 μg/L thiamine and 200 r/min, respectively;

(3) producing the extremely high-optical pure D-lactic acid by fermentation, wherein the fermentation temperature of oxygen limiting stage 0-3 h is 33-39° C., the fermentation temperature of 3-6 h is 37-42° C., the fermentation temperature of 6-10 h is 38-45° C., the fermentation temperature of 10-16 h is 40-48° C., and the fermentation temperature of 16-24 h is 45-50° C.;

(3') producing the extremely high optical pure L-lactic acid by fermentation, the fermentation temperature of oxygen limiting stage is 37-50° C., the rest is the same as step (3).

Preferably, the method for manufacturing lactic acid above mentioned, also comprises an extraction method of lactic acid after fermentation. Considering the characteristics of producing strain after being genetically engineered, both the D-lactic acid and the L-lactic acid in the fermentation broth are in the form of extremely high optical pure and extremely high chemical pure, the use of total-synthetic medium ensures the post-extraction process to be simple. The extraction method of the final product comprises acidification, filtration by plate frame to remove thallus, ultrafiltration to remove pigment and impure protein, ion exchange to remove interference of anions and cations, concentration to get a product with a corresponding concentration, nanofiltration and refining on the product and other process links.

Preferably, in the method for manufacturing lactic acid above mentioned, after the lactic acid forming process is finished, D-lactic acid and L-lactic acid are freed by a low-temperature acidification, and the freeing process of the lactic acid is not affected by other residues in the fermentation broth, the acid used for acidification can be selected from one of the group consisting of sulfuric acid, hydrochloric acid and oxalic acid, and more preferably sulfuric acid.

In the method for manufacturing lactic acid above mentioned, the extremely high optical pure D-lactic acid and L-lactic acid produced by fermentation process takes less than 30-36 h, the yield of D-lactic acid and L-lactic acid are respectively 150 g/L and 180 g/L or more, the optical purity of the D-lactic acid and L-lactic acid are both more than 99.95%, and the chemical purity of them are more than 97%.

The method for manufacturing lactic acid above mentioned, also comprises other chemicals with similar reaction processes, such as citric acid, formic acid, acetic acid, pyruvic acid, succinic acid, malic acid, α-ketoglutaric acid, succinic acid, adipic acid, glutaric diamine, hexamethylenediamine, methacrylic acid, isoprene, itaconic acid and other organic acids and organic amines; or proline, alanine, lysine, methionine, glutamic acid, arginine and the like: thiamine, vitamin $B_{12}$ and the like; or ethanol, propanol and other short-chain alcohol; or isomalto-oligosaccharide, fructo-oligosaccharide, galactooligosaccharide and other functional sugars.

The present disclosure has the following beneficial effects:

On the basis of ZL201210102731.8 which greatly improved the synthesis efficiency of the D-lactic acid by introducing a temperature regulation element in the gene transcription level and matching with a fermentation temperature control strategy, the present disclosure introduced a regulation mechanism of cell growth quantity control, and a double-switch mechanism of cell growth process and D-lactic acid synthesis process is formed, resulting in further improvement of the D-lactic acid synthesis efficiency. The extremely high optical pure L-lactic acid producing strain in the present disclosure makes full use of the enzymatic properties of exogenous L-lactate dehydrogenase after being translated and expressed, and introduces a temperature regulation mechanism of its catalytic activity, and then the double-switch mechanism of cell growth process and D-lactic acid synthesis was completed coordinating with the regulation mechanism of cell growth quantity control.

More prominently, the large-scale production of two products in the same system can be performed by switching the producing strains of the process of extremely high optical pure D-lactic acid and L-lactic acid disclosed in the invention.

Specific benefits are as follows:

1. The recombinant strains provided by the present disclosure have obvious capability of efficiently synthesizing extremely high optical pure D-lactic acid and L-lactic acid, and meanwhile, the recombinant strains possess the capability of synthesizing D-lactic acid and L-lactic acid with high chemical purity. The strains grow rapidly for 8-10 hours at 25-50° C., then fermentation is done to produce acid for 16-18 hours, and the yield of the D-lactic acid is up to 15% (w/v) or more, and the yield of L-lactic acid reaches 18% (w/v) or more;

2. The total-synthesis medium is adopted in the fermentation process by the recombinant strains provided by the present disclosure which can efficiently synthesize the extremely high optical pure lactic acid monomer, which made the fermentation broth clear, and the separation and extraction of subsequent products facilitated;

3. The growth and acid fermentation process of the recombinant strains provided by the present disclosure which can efficiently synthesize the extremely high optical pure lactic acid monomer can be efficiently controlled by temperature variations;

4. The growth and acid fermentation process of the recombinant strains provided by the present disclosure which can efficiently synthesize the extremely high optical pure lactic acid monomer can be subject to quantitative and on-off control by adding nutrients;

5. The preparation process of the extremely high optical pure lactic acid monomer provided by the present disclosure shows: strains grow rapidly for 6-12 hours at 25-36° C. with glucose, so as to form thallus; then rapidly synthesize the extremely high optical-pure D-lactic acid and L-lactic acid at 37-50° C. with glucose. Namely, the use of the recombinant strains and preparation technology provided by the present disclosure can carry out an efficient preparation process of the extremely high optical pure D-lactic acid and L-lactic acid only by changing the fermentation temperature and adding nutrients.

DEPOSIT INFORMATION

Figure 1:
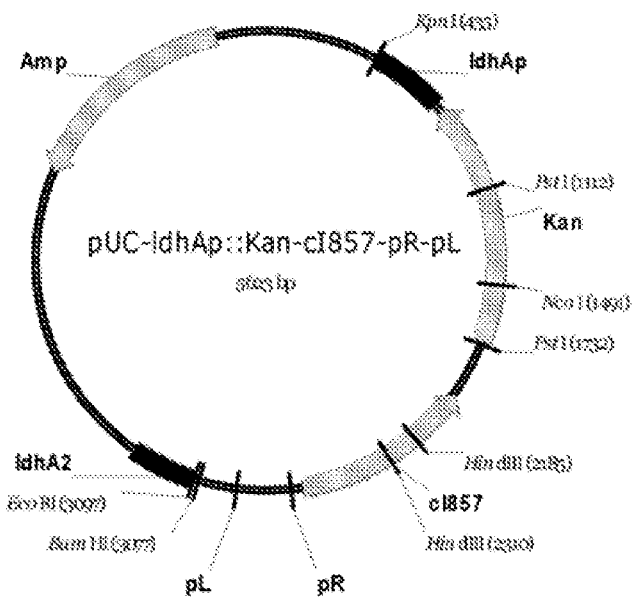
FIG. 1 Physical map of mutant cassette pUC-ldhAp::kan-clts857-pR-pL.

Classification name: *Escherichia coli*
Deposit institution: China General Microbiological Culture Collection Deposit institution address: No. 3, Yard No. 1, Beichen West Road, Chaoyang District, Beijing
Deposit data: Jul. 7, 2015
Deposit number: CGMCC No. 11059
Reference biomaterial (strain): B0013-090B
[The strain was deposited at CGMCC under the Budapest Treaty and will be made available to the public upon issuance of a patent.]
Classification name: *Escherichia coli*
Deposit institution: China General Microbiological Culture Collection Deposit institution address: No. 3, Yard No. 1, Beichen West Road, Chaoyang District, Beijing
Deposit data: Jul. 7, 2015
Deposit number: CGMCC No. 11060
Reference biomaterial (strain): B0013-101J
[The strain was deposited at CGMCC under the Budapest Treaty and will be made available to the public upon issuance of a patent.]

DETAILED DESCRIPTION

The technical schemes of the present disclosure are further described below with reference to specific examples.

A extremely high optical pure D-lactic acid producing strain and a extremely high optical pure L-lactic acid producing strain, the construction method thereof, and the high-efficiency preparation process of the extremely high optical pure D-lactic acid and L-lactic are provided in the present disclosure, the strain grow rapidly at 25-36° C. with glucose to form high-activity cells, then accumulate the extremely high optical pure D-lactic acid and L-lactic at 37-50° C., and the chemical purity of the accumulated lactic acid is extremely high. The preparation method is characterized that: strains experienced a cultivation stage and a temperature-variable high-efficiency acid production stage at 25-50° C., the yield of D-lactic acid is up to 15% (w/v) or more, the optical purity is more than 99.9%, the chemical purity is more than 97%; the yield of L-lactic acid is up to 18% (w/v) or more, the optical purity is more than 99.9%, the chemical purity is more than 98%.

The invention relates to a specific method:

Chromosome gene integration technology: the upstream and downstream gene sequences about 50-700 bp of the target integration site on chromosome are amplified by PCR from the genome of *E. coli*. The target integrated expression gene is ligated with the resistance gene, and the obtained fragment is cloned into a position between the upstream gene sequence and the downstream gene sequence of the target integration site to form target gene integration sequences, e.g. ldhAp:: kan-clts857-pR-pL; thiE':: difGm; dld':: difGm; ackA-pta':: difGm; pps':: difGm; pflB':: difGm; poxB':: difGm; frdA':: difGm; adhE':: difGm; ldhA':: difGm; lldD'::PldhA-ldhBcoa-difGm; lldD'::PldhA-ldhLca-difGm; lldD'::PldhA-ldhStrb-difGm; ldhA'::PldhA-ldhLca-difGm; ldhA'::PldhA-ldhStrb-difGm; thiE'::PldhA-ldhLca-difGm; thiE'::PldhA-ldhStrb-difGm; thiE'::PldhA-ldhBcoa-difGm. The gene integration sequences are transformed into *E. coli* independently or in any combination of two or more. Transformants are selected from the selective medium. Chromosome DNA of the transformants is extracted, then the target gene mutation of the transformant is verified by PCR. The optimal extremely high optical pure D-lactic acid high-yield strain such as B0013-090B and extremely high optical pure L-lactic acid high-yield strain such as B0013-101J is screened by virtue of a fermentation test.

The construction of a dynamically regulated D-lactic acid production recombinant strain is carried out according to the following steps with the recombinant method above mentioned.

1. Strain for research: *E. coli* B0013 (Zhou L. et al., Curr Microbiol, 2011, 62: 981-989), 2. The promoter of the lactate dehydrogenase gene in the starting strain obtained in step 1 was replaced from ldhAp to pR-pL (Love C. A. et al., Gene, 1996, 176:49-53) by the gene integration technology, and a recombinant *E. coli* 1 is obtained.

3. The mutant cassette thiE':: difGm used for deleting the encoding gene of thiamine phosphate synthase (thiE) is constructed by using the gene integration technology, and then a recombinant *E. coli* 2 is obtained after deleting the thiE gene of recombinant strain obtained in step 2.

4. The mutant cassette dld':: difGm used for deleting the encoding gene of FDA-dependent D-lactate dehydrogenase (dld) is constructed by using the gene integration technology, and then a recombinant *E. coli* 3 is obtained by deleting the dld gene of recombinant strain obtained in step 3.

5. The mutant cassette ackA-pta'::difGm used for deleting the encoding gene of acetokinase (ackA) and phosphotransacetylase (pta) is constructed by using the gene integration technology, and a recombinant *E. coli* 4 is obtained by deleting the ackA-pta gene of recombinant strain obtained in step 4.

6. The mutant cassette pps'::difGm used for deleting the encoding gene of phosphoenol pyruvate synthase (pps) is constructed by using the gene integration technology, and a recombinant *E. coli* 5 and 6 are obtained by deleting the pps gene of recombinant strain obtained in step 4 and 5.

7. The mutant cassette pflB'::difGm used for deleting the encoding gene of pyruvate formate-lyase (pflB) is constructed by using the gene integration technology, and a recombinant *E. coli* 7-10 are obtained by deleting the pflB gene of recombinant strain obtained in step 4, 5 and 6.

8. The mutant cassette poxB'::difGm used for deleting the encoding gene of pyruvic oxidase (poxB) is constructed by using the gene integration technology, a recombinant *E. coli* 11-18 are obtained by deleting the poxB gene of recombinant strain obtained in step 4, 5, 6 and 7.

9. The mutant cassette frdA'::difGm used for deleting the encoding gene of fumaric reductase (frdA) is constructed by using the gene integration technology, a recombinant *E. coli* 19-34 is obtained by deleting the frdA gene of recombinant strain obtained in steps 5, 6, 7 and 8.

10. The mutant cassette adhE'::difGm used for deleting the encoding gene of ethanol dehydrogenase (adhE) is constructed by using the gene integration technology, a recombinant *E. coli* 35-66 is obtained by deleting the adhE gene of recombinant strain obtained in step 4, 5, 6, 7, 8 and 9.

11. The mutant cassette ldhA'::difGm used for deleting the encoding gene of D-lactate dehydrogenase (ldhA) is constructed by using the gene integration technology, a recombinant *E. coli* 67 is obtained by deleting the ldhA gene of recombinant strain B0013-070.

12, The mutant cassette ldhA'::PldhA-ldhLca-difGm used for deleting the encoding gene of D-lactate dehydrogenase (ldhA) is constructed by using the gene integration technology, a recombinant *E. coli* 68 is obtained by deleting the ldhA gene of recombinant strain B0013-070.

13. The mutant cassette ldhA'::PldhA-ldhStrb-difGm used for deleting the encoding gene of D-lactate dehydrogenase (ldhA) is constructed by using the gene integration technology, a recombinant *E. coli* 69 is obtained by deleting the ldhA gene of recombinant strain B0013-070.

14. The mutant cassette lldD'::PldhA-ldhBcoa-difGm used for deleting the encoding gene of L-lactic dehydrogenase (lldD) which take FMN as coenzyme is constructed by using the gene integration technology, a recombinant *E. coli* 70-73 are obtained by deleting the lldD gene of recombinant strain B0013-070 and recombinant strains obtained in step 11, 12 and 13.

15. The mutant cassette lldD'::PldhA-ldhLca-difGm used for deleting the encoding gene of L-lactic dehydrogenase (lldD) which take FMN as coenzyme is constructed by using the gene integration technology, a recombinant *E. coli* 74-77 are obtained by deleting the lldD gene of recombinant strain B0013-070 and recombinant strains obtained in step 11, 12, 13 and B0013-170.

16. The mutant cassette lldD'::PldhA-ldhBcoa-difGm used for deleting the encoding gene of L-lactate dehydrogenase (lldD) which take FMN as coenzyme is constructed by using the gene integration technology, a recombinant *E. coli* 74-77 are obtained by deleting the lldD gene of recombinant strain B0013-070 and recombinant strains obtained in step 11, 12 and 13.

17. The mutant cassette thiE':: difGm used for deleting the encoding gene of thiamine phosphate synthase (thiE) is constructed by using the gene integration technology, a recombinant *E. coli* 82-96 are obtained by deleting the thiE gene of recombinant strains obtained in step 11, 12, 13, 14, 15 and 16.

18. The mutant cassette thiE'::PldhA-ldhLca-difGm used for deleting the encoding gene of thiamine phosphate synthase (thiE) is constructed by using the gene integration technology, a recombinant *E. coli* 97-111 are obtained by deleting the thiE gene of recombinant strains obtained in step 11, 12, 13, 14, 15 and 16.

19. The mutant cassette thiE'::PldhA-ldhStrb-difGm used for deleting the encoding gene of thiamine phosphate synthase (thiE) is constructed by using the gene integration technology, a recombinant *E. coli* 112-126 are obtained by deleting the INF gene of recombinant strain obtained in step 11, 12, 13, 14, 15 and 16.

20. The mutant cassette thiE'::PldhA-ldhBcoa-difGm used for deleting the encoding gene of thiamine phosphate synthase (thiE) is constructed by using the gene integration technology, a recombinant *E. coli* 127-156 are obtained by deleting the thiE gene of recombinant strain obtained in steps 11, 12, 13, 14, 15 and 16.

21. The recombinant strains obtained in steps 4, 5, 6, 7, 8, 9, 10, 11, 12, 13, 14, 15, 16, 17, 18, 19 and 20 are subjected to shake flask culture at 200 r/min, 30° C. and 45° C., and the starting strain B0013-070 is used as a control to analyze specific activity of lysine dehydrogenase, identify the functions of the $p_R$-$p_L$ promoter and thiE, and screen out the optimal strains.

22. The optimal strains obtained in step 21 are subjected to shake flask culture at the 25-36° C. and 200 r/min respectively, and the starting strain B0013-070 is used as a control strain to analyze the cell density, the lactic acid, metabolic main intermediates, other organic acid products and the like, and then the growth culture temperature of the strains are determined.

23. The optimal strains obtained in step 21 are aerobically cultured at 25-36° C., and 200 r/min for 6-10 h firstly, then the lactic acid fermentation is carried out by stationary culture at 37-45° C., and the starting strain B0013-070 is used as a control to analyze the cell density, sugar consumption, productivity of lactic acid, main metabolic intermediates, other organic acid products and the like, to determine the induction time of lactic acid synthesis.

24. The optimal strains obtained in above step are subjected to shake flask culture with 0.06-100 µg/L thiamine at 200 r/min respectively, and the starting strain B0013-070 is used as a control to analyze the cell density, the lactic acid, metabolic main intermediates, other organic acid products and the like, to determine the addition amount of the thiamine.

25. The lactic acid fermentation of the optimal strains obtained in the step 20 are carried out in 7 L-30,000 L fermentation tanks, and the starting strain B0013-070 is used as a control to analyze the cell density, sugar consumption, productivity of lactic acid, main metabolic intermediates, other organic acid products and the like by timing sampling during a fermentation process.

The technical solution of the present disclosure is described in further detail below with specific examples.

Example 1—Construction of Mutant Cassette ldhA::kan-clts857-pR-pL

An ldhA gene segment ldhA' on a chromosome of B0013 is amplified by primers ldhA1 and ldhA2 through PCR (polymerase chain reaction), and introduced into a carrier pUC18 by cloning, to obtain a recombinant plasmid pUC-ldhA'. The plasmid pP451 is subjected to a reverse PCR amplification by primers PPL1 and PPL2, and then ligated to a kanamycin resistance gene segment (plasmid pSK-symKm is subjected to enzyme digestion by SmaI, and gel recycle 966 bp segment), to obtain a recombinant plasmid pPL-Kan. The plasmid pPL-kan is subjected to a PCR amplification by using primers PPL3 and PPL4. And then the resulting product is subjected to double digestion by EcoRI and EcoRV, (and ligated to the product which obtained by a reverse PCR amplification with the pUC-ldhA' as a template by using primers Ec-R1A1 and Ec-R1A2, and enzyme digestion by using EcoRI), thus to obtain a recombinant plasmid pUC-ldhAp::kan-clts857-pR-pL. The physical map of the obtained recombinant plasmid is shown in FIG. 1. The recombinant plasmid pUC-ldhAp::kan-clts857-pR-pL is subjected to enzyme digestion by KpnI, and the linearized plasmids are recycled through glue extraction. Then a gene segment ldhAp:: kan-clts857-pR-pL is obtained following a PCR amplification with ldhA1 and ldhA2 as primers.

Example 2—Construction of Mutant Cassette thiE::difGm

Figure 2:
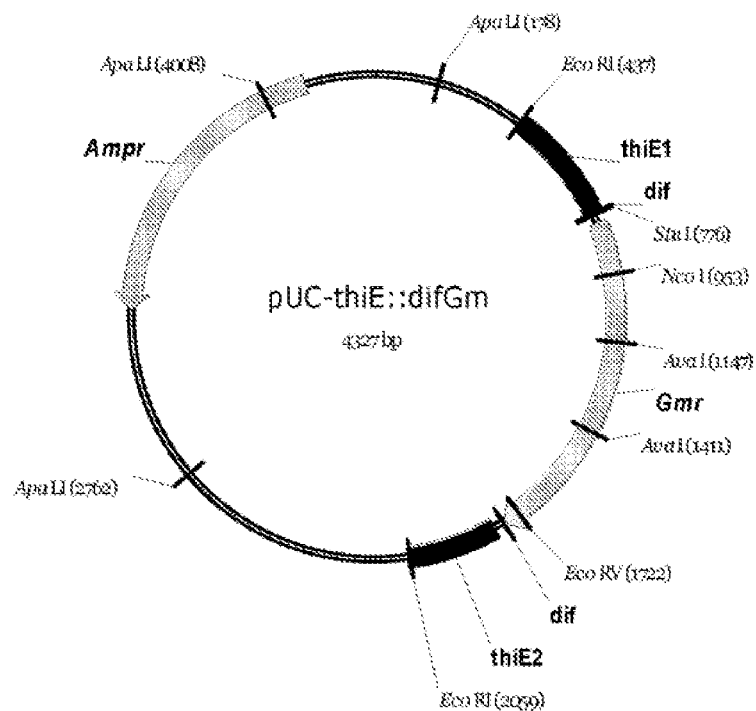
FIG. 2 Physical map of mutant cassette pUC-thiE':: difGm.

A thiE gene part sequence with a length of 0.6 kb is obtained by an amplification using the *E. coli*. B0013 chromosome DNA as the template and ThiE1p and ThiE2p as primers. And then it is introduced into pUC18 by cloning, to obtain a recombinant plasmid pUC-thiE. A difGm segment with length of 1.2 kb is introduced to StuI site in the middle of the thiE by cloning, to obtain a recombinant plasmid pUC-thiE::difGm. The physical map of the recombinant plasmid pUC-thiE::difGm is shown in FIG. 2. The recombinant plasmid is subjected to enzyme digestion by ApaLI, and the linearized plasmids are recycled through glue extraction. Then a gene segment thiE::difGm is obtained following a PCR amplification by using ThiE1p and ThiE2p as primers.

Example 3—Construction of Mutant Cassette dld::difGm

Figure 3:
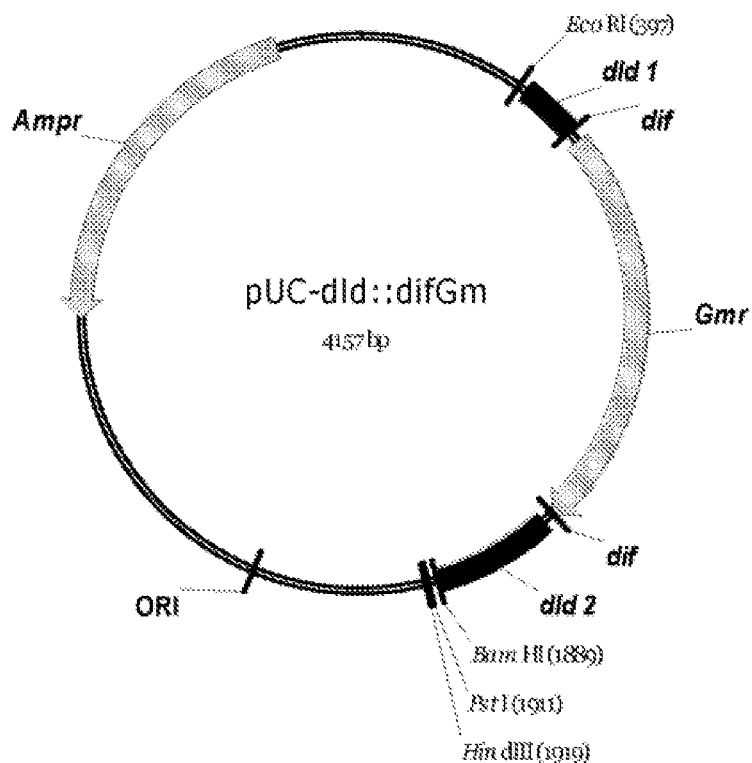
FIG. 3 Physical map of mutant cassette pUC-dld':: difGm.

A dld' gene segment (0.9 kb) is obtained by a PCR amplification using strain B0013 chromosome DNA as the template and Dld1 and Dld2 as primers. The resulting PCR product is introduced to the SmaI site of vector pUC18 by cloning, to obtain a recombinant plasmid pUC-dld'. Then, the recombinant plasmid pUC-dld' is subjected to an enzyme digestion by EcoRV, and a 0.4 kb gene segment in the middle of dld' gene is removed and replaced into a dif-Gm-dif segment by cloning to obtain a recombinant plasmid pUC-dld'::difGm. The physical map of the recombinant plasmid is shown in FIG. 3. The recombinant plasmid pUC-dld':: difGm is subjected to enzyme digestion by EcoRI, and the linearized plasmids are recycled through glue extraction. Then a gene segment dld'::difGm is obtained following a PCR amplification by using Dld1 and Dld2 as primers.

Example 4—Construction of Mutant Cassette ackA-pta::difGm

Figure 4:
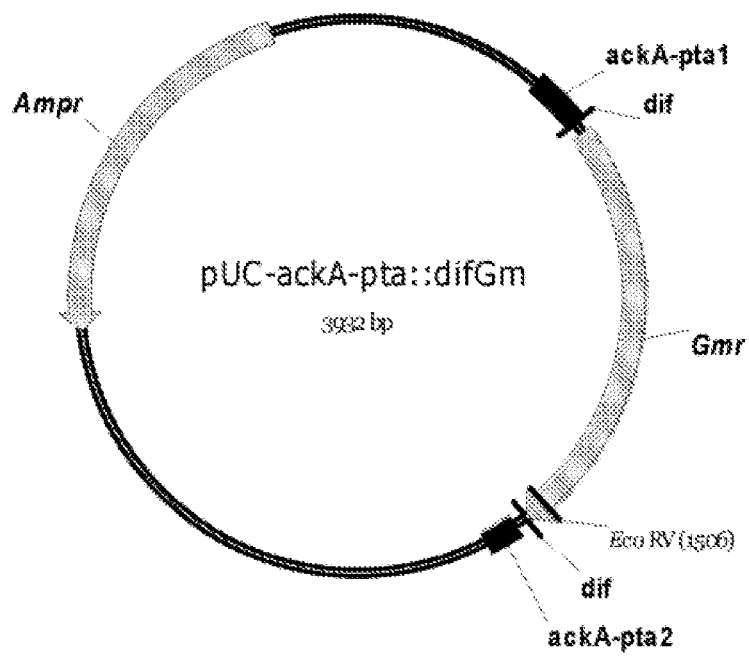
FIG. 4 Physical map of mutant cassette pUC-ackA-pta':: difGm.

An ackA-pta' gene segment (2.8 kb) is obtained by a PCR amplification using strain B0013 chromosome DNA as the template and AckA-Pta1 and AckA-Pta2 as primers. The PCR product is introduced to a vector pUC18 by cloning, to obtain a recombinant plasmid pUC-ackA-pta'. Then, the recombinant plasmid pUC-ackA-pta' is subjected to an enzyme digestion by EcoRV, and a 2.6 kb gene segment in the middle of ackA-pta' gene is removed and replaced into a dif-Gm-dif segment by cloning to obtain a recombinant plasmid pUC-ackA-pta'::difGm. The physical map of the recombinant plasmid is shown in FIG. 4. The recombinant plasmid pUC-ackA-pta'::difGm is subjected to enzyme digestion by KpnI, and the linearized plasmids are recycled through glue extraction. Then a gene segment ackA-pta':: difGm is obtained following a PCR amplification by using AckA-Pta1 and AckA-Pta2 as primers.

Example 5—Construction of Mutant Cassette pps::difGm

Figure 5:
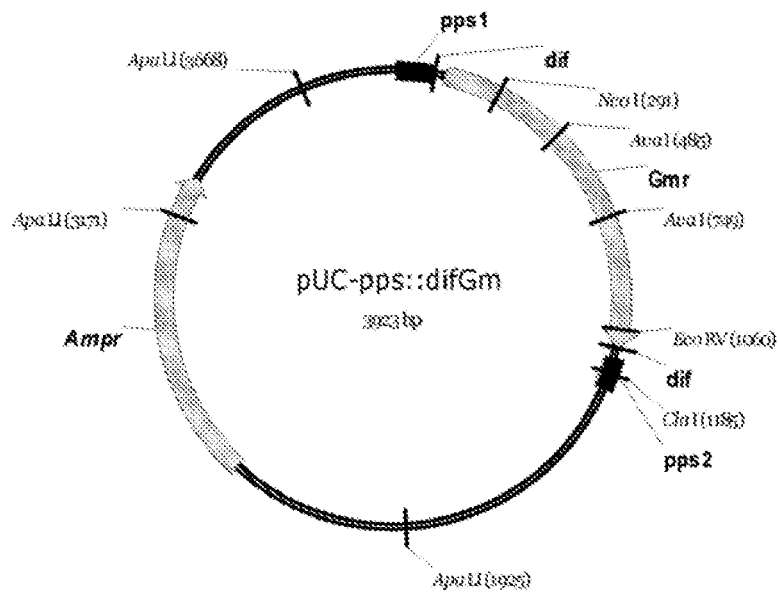
FIG. 5 Physical map of mutant cassette pUC-pps'::difGm.

A pps gene segment (2.3 kb) is obtained by a PCR amplification using strain B0013 chromosome DNA as the template and Pps1 and Pps2 as primers. The PCR product is introduced to a vector pUC18 by cloning, to obtain a recombinant plasmid pUC-pps'. Then, a reverse PCR amplification is carried out using the plasmid pUC-pps' as a template and RPps1 and RPps2 as primers, and a 2.1 kb gene segment in the middle of pps' gene was removed and replaced into a dig-Gm-dif segment by cloning to obtain a recombinant plasmid pUC-pps'::difGm. The physical map of the recombinant plasmid is shown in FIG. 5. The recombinant plasmid pUC-pps'::difGm is subjected to enzyme digestion by ApaLI, and the linearized plasmids are recycled through glue extraction. Then a gene segment pps'::difGm is obtained following a PCR amplification by using Pps1 and Pps2 as primers.

Example 6—Construction of Mutant Cassette pflB::difGm

Figure 6:
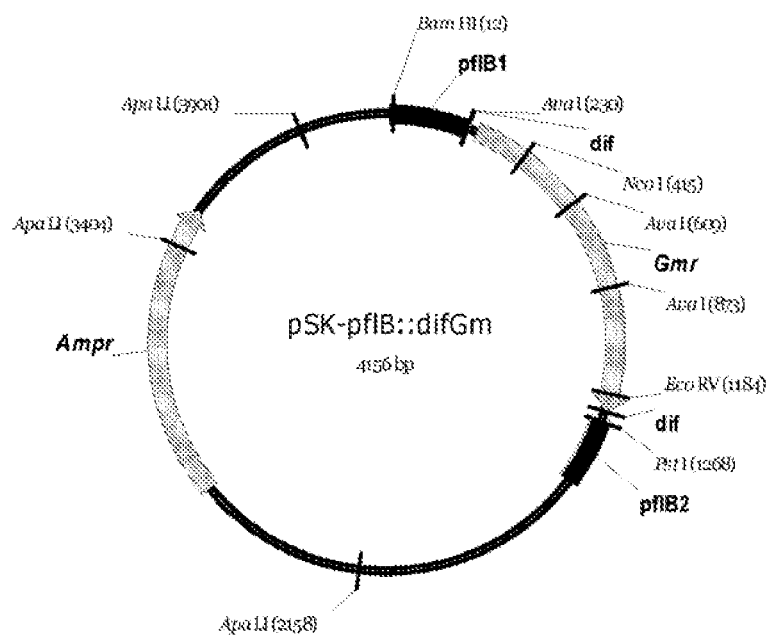
FIG. 6 Physical map of mutant cassette pSK-pflB':: difGm.

A PCR amplification is carried out using strain B0013 chromosome DNA as a template and PflB1 and PflB2 as primers. The resulting product PflB' is introduced to EcoRV and SmaI site of vector pSK by cloning (during this process, PstI and EcoRI disappeared) to obtain a recombinant plasmid pSK-pflB'. The plasmid pSK-pflB' is subjected to an enzyme digestion by PstI, then an filling-in is ligated to difGm in the pSK-EcdifGm to obtain a recombinant plasmid pSK-pflB'::difGm. The physical map of the obtained recombinant plasmid is shown in FIG. 6. The recombinant plasmid pSK-pflB'::difGm is subjected to a digestion by ApaLI, and the linearized plasmids are recycled through glue extraction. Then a gene segment pflB'::difGm is obtained following a PCR amplification by using PflB1 and PflB2 as primers.

Example 7—Construction of Mutant Cassette poxB::difGm

Figure 7:
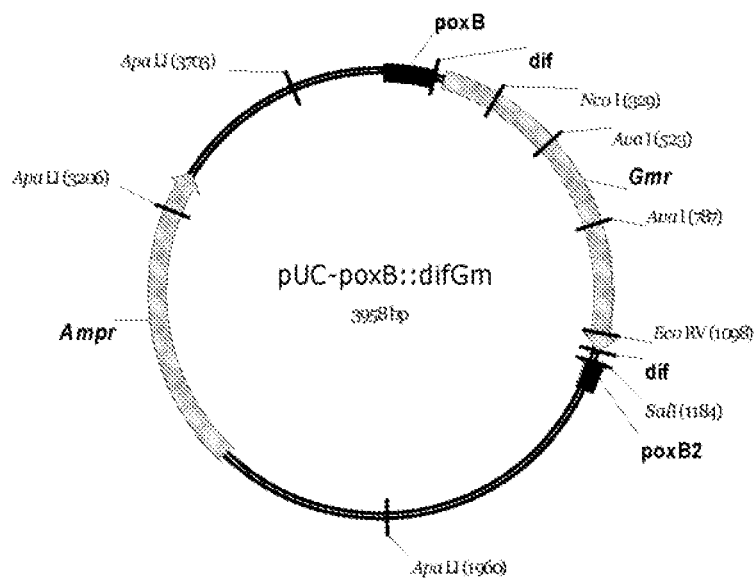
FIG. 7 Physical map of mutant cassette pUC-poxB':: difGm.

A poxB gene segment of *E. coli* is amplified by using PoxB1 and PoxB2 as primers, the PCR product is introduced to a SmaI site of vector pUC18 by cloning, to obtain a recombinant plasmid pUC-poxB'. Then, the recombinant plasmid pUC-poxB' is subjected to an enzyme digestion by EcoRV, and introduced into a dif-Gm segment by cloning to obtain a recombinant plasmid pUC-poxB'::difGm. The physical map of the recombinant plasmid is shown in FIG. 7. The recombinant plasmid pUC-poxB'::difGm is subjected to enzyme digestion by ApaLI, and the linearized plasmids are recycled through glue extraction. Then a gene segment poxB'::difGm is obtained following a PCR amplification by using PoxB1 and PoxB2 as primers.

Example 8—Construction of Mutant Cassette frdA:: difGm

Figure 8:
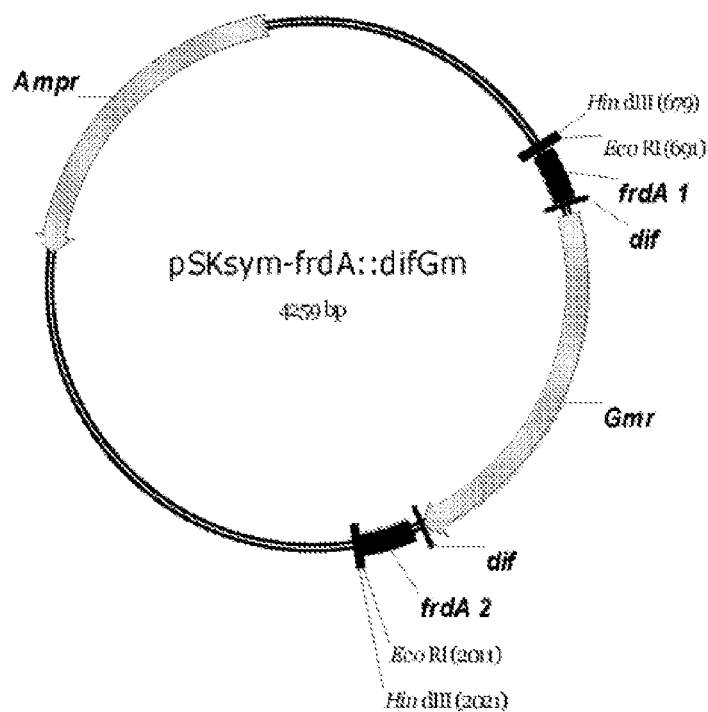
FIG. 8 Physical map of mutant cassette pSKsym-frdA':: difGm.

A frdA' gene segment (1.6 kb) is obtained by a PCR amplification using strain B0013 chromosome DNA as the template and FrdA1 and FrdA2 as primers. The PCR product is introduced to the SmaI site of vector pSKsym by cloning, to obtain a recombinant plasmid pSKsym-frdA'. Then, the recombinant plasmid pSKsym-frdA' is subjected to an enzyme digestion by PstI, a 1.3 kb gene segment in the middle of frdA' is removed, smoothing the sticky tail end of the PstI by using a T4 DNA polymerase, and introducing into a dif-Gm-dif segment by cloning, so that a recombinant plasmid pSKsym-frdA'::difGm is obtained. The physical map of the recombinant plasmid is shown in FIG. 8. The recombinant plasmid pSKsym-frdA'::difGm is subjected to enzyme digestion by ApaLI, and the linearized plasmids are recycled through glue extraction. Then a gene segment frdA'::difGm is obtained following a PCR amplification by using FrdA1 and FrdA2 as primers.

Example 9—Construction of Mutant Cassette adhE: difGm

Figure 9:
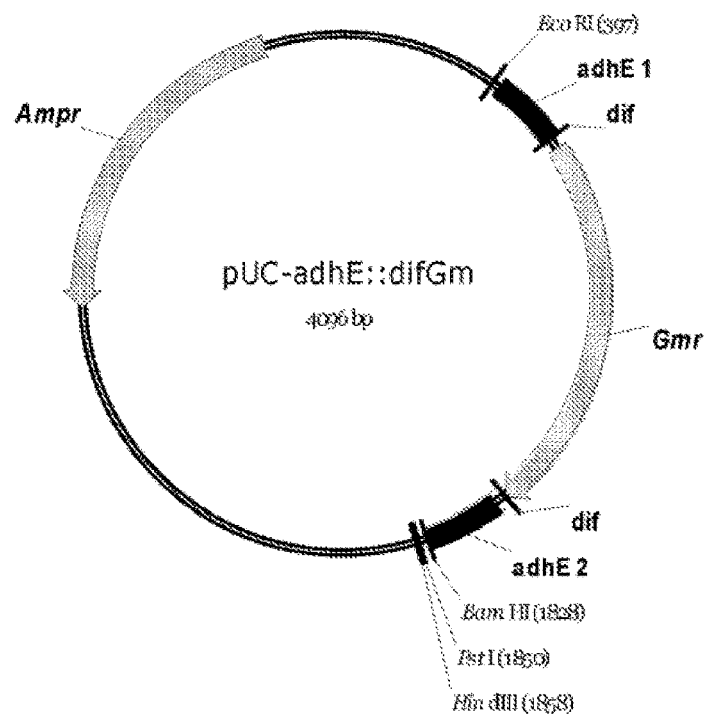
FIG. 9 Physical map of mutant cassette pUC-adhE':: difGm.

An adhE' gene segment (1.4 kb) is obtained by a PCR amplification using strain B0013 chromosome DNA as the template and AdhE1 and AdhE2 as primers. The PCR product is introduced to a vector pUC19 SmaI site by cloning, to obtain a recombinant plasmid pUC-adhE'. Then, the recombinant plasmid pUC-adhE' is subjected to an enzyme digestion by EcoRV, a 1 kb gene segment in the middle of adhE' is removed, and introduced into a dif-Gm-dif segment is by cloning, so that a recombinant plasmid pUC-adhE'::difGm is obtained. The physical map of the recombinant plasmid is shown in FIG. 9. The recombinant plasmid pUC-adhE'::difGm is subjected to a double digestion by EcoRI and PstI, and a segment adhE1-dif-Gm-dif-adhE2 is recycled.

Example 10—Construction of Mutant Cassette ldhA::difGm

Figure 10:
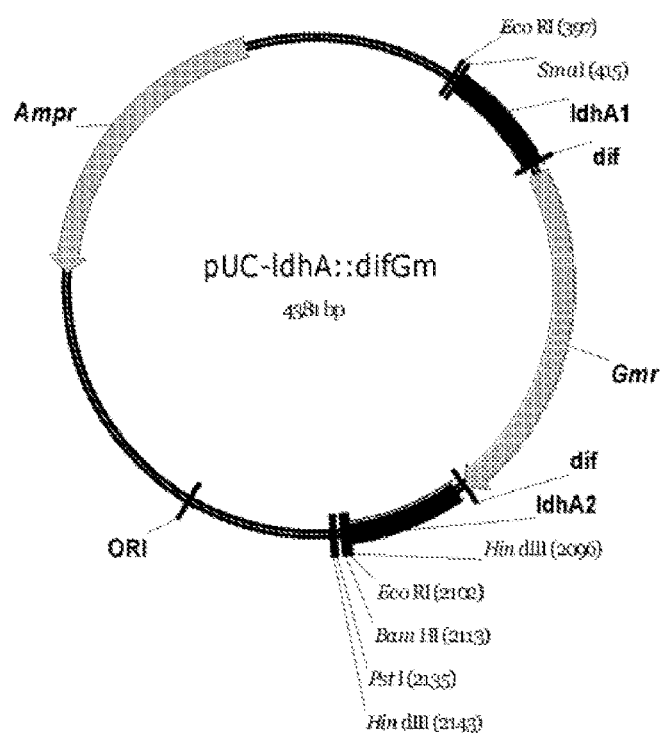
FIG. 10 Physical map of mutant cassette pUC-ldhA:: difGm.

A ldhA gene is obtained by a PCR amplification using the *E. coli* strain B0013 chromosome DNA as a template and ldhA1 and ldhA2 as primers. The resulting product is introduced to EcoRI site of vector pUC18 by cloning to obtain a recombinant plasmid pUC-ldhA. A 400 bps segment is removed by digestion using PstI, and a filing-in with T4 DNA polymerase is carried out on the sticky tail end, then the resulting product is ligated to difGm segment to obtain a recombinant plasmid pUC-ldhA::Gmdif. The physical map of the obtained recombinant plasmid is shown in FIG. 10. The recombinant plasmid is subjected to a digestion by EcoRI, then a ldhA deleting segment ldhA'-dif-Gm-dif-ldA is obtained, that is ldhA::Gmdif.

Example 11—Construction of Mutant Cassette lldD::PldhA-ldhBcoa-difGm

Figure 11:
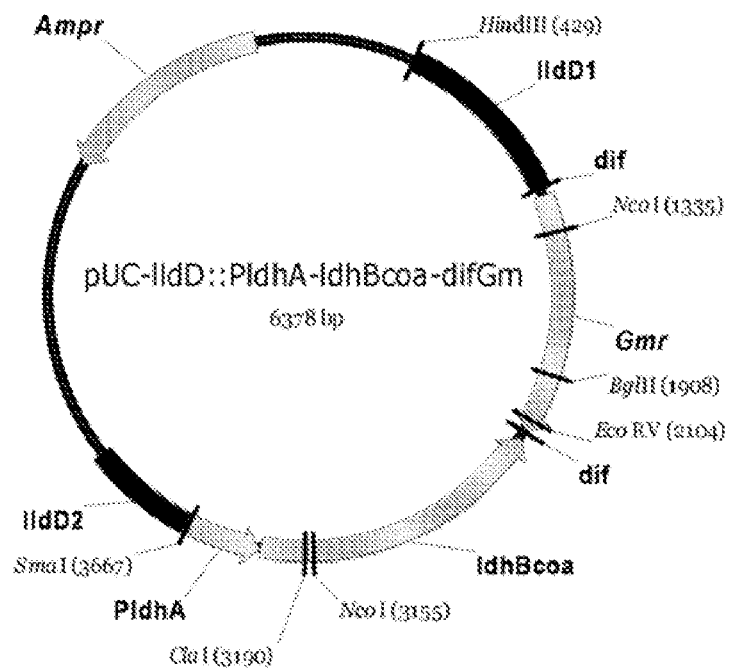
FIG. 11 Physical map of mutant cassette pUC-lldD':: PldhA-ldhBcoa-difGm.

An amplification (ldhA5 and ldhA6 as primers) is carried out using *E. coli* strain B0013 chromosome DNA as a template to obtain all promoters and partial structural region fragments of the ldhA gene, and the segment ldhA' is introduced to the vector pUC18 by cloning to obtain a recombinant plasmid pUC-ldhA'. A reverse PCR amplification is carried out using the plasmid pUUC-ldhA' as a template and RldhA1 and RldhA2 as primers, and a self-link is carried out between the products, then a recombinant plasmid pUC-PldhA is obtained. A PCR amplification is carried out using *Bacillus* coagulants CICIM B1821 chromosome DNA as a template to obtain the ldhBcoa gene segment. After digestion by BamHI and EcoRI, it is introduced to BglII and EcoRI of pUC-PldhA' to obtain a recombinant plasmid pUC-PldhA-ldhBcoa. Then, the difGm segment is introduced to the EcoRV site of the recombinant plasmid pUC-PldhA-ldhBcoa, to obtain a recombinant plasmid pUC-PldhA-ldhBcoa-difGm. A lldD gene segment is obtained by PCR amplification (primers are lldD1 and lldD2), and is introduced to a sub-cloning vector pUC18 to obtain a recombinant plasmid pUC-lldD. A PldhA-ldhBcoa-difGm segment is obtained from the recombinant plasmid pUC-PldhA-ldhBcoa-difGm by digestion using BamHI, and is introduced to the BamHI site of the recombinant plasmid pUC-lldD to obtain a recombinant plasmid pUC-lldD::PldhA-ldhBcoa-difGm. The physical map of the recombinant plasmid is shown in FIG. 11. The recombinant plasmid pUC-lldD::PldhA-ldhBcoa-difGm is digested by SmaI, and a lldD::PldhA-ldhBcoa-difGm gene segment is obtained by glue extraction.

Example 12—Construction of Mutant Cassette lldD:PldhA-ldhLca-difGm

An amplification (ldhA5 and ldhA6 as primers) is carried out using *E. coli* CICIM B0013 chromosome DNA as a template to obtain all promoters and partial structural region fragments of the ldhA gene, and the segment ldhA' is introduced to the vector pUC18 by cloning to obtain a recombinant plasmid pUC-ldhA'. A reverse PCR amplification is carried out using the plasmid pUC-ldhA' as a template and RldhA1 and RldhA2 as primers, and a self-link is carried out between the products, then a recombinant plasmid pUC-PldhA is obtained. A PCR amplification (LcaLDH1 and LcaLDH4 as primers) is carried out using *Lactobacillus casei* B1192 chromosome DNA as a template to obtain the ldhLca gene segment. After digestion by BamHI and EcoRI, it is introduced to BglII and PstI of pUC-PldhA' to obtain a recombinant plasmid pUC-PldhA-ldhLca. Then, the difGm segment is introduced to the EcoRV site of the recombinant plasmid pUC-PldhA-ldhLca, to obtain a recombinant plasmid pUC-PldhA-ldhLca-difGm.

Figure 12:
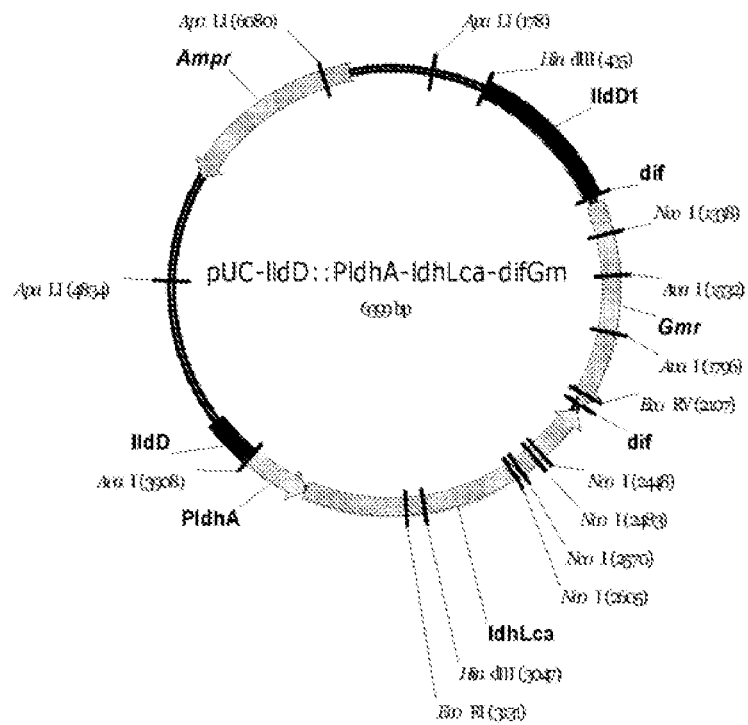
FIG. 12 Physical map of mutant cassette pUC-lldD':: PldhA-ldhLca-difGm.

A lldD gene segment is obtained by PCR amplification (primers are lldD1 and lldD2), and is introduced to a sub-cloning vector pUC18 to obtain a recombinant plasmid pUC-lldD. A PldhA-ldhLca-difGm segment is obtained from the recombinant plasmid pUC-PldhA-ldhLca-difGm by digestion using BamHI, and is introduced to the BamHI site of the recombinant plasmid pUC-lldD to obtain a recombinant plasmid pUC-lldD::PldhA-ldhLca-difGm. The physical map of the recombinant plasmid is shown in FIG. 12. The recombinant plasmid pUC-lldD::PldhA-ldhLca-difGm is digested by SmaI, and a lldD::PldhA-ldhLca-difGm gene segment is obtained by glue extraction.

Example 13—Construction of Mutant Cassette lldD:PldhA-ldhStrb-difGm

A PCR amplification (ldhA5 and ldhA6 as primers) is carried out using *E. coli* CICIM B0013 chromosome DNA as a template to obtain all promoters and partial structural region fragments of the ldhA gene. And the segment ldhA' is introduced to the vector pUC18 by cloning to obtain a recombinant plasmid pUC-ldhA'. A reverse PCR amplification is carried out using the plasmid pUC-ldhA' as a template and RldhA1 and RldhA2 as primers, and a self-link is carried out between the products, then a recombinant plasmid pUC-PldhA is obtained. A PCR amplification (StrbLDH1 and StrbLDH2 as primers) is carried out using *Steptococcus. bovis* 1.1624 chromosome DNA as a template to obtain the ldhStrb gene segment. After digestion by BamHI and EcoRI, it is introduced to BglII and EcoRI of pUC-PldhA' to obtain a recombinant plasmid pUC-PldhA-ldhStrb. Then, the difGm segment is introduced to the EcoRV site of the recombinant plasmid pUC-PldhA-ldhStrb, to obtain a recombinant plasmid pUC-PldhA-ldhBcoa-difGm.

Figure 13:
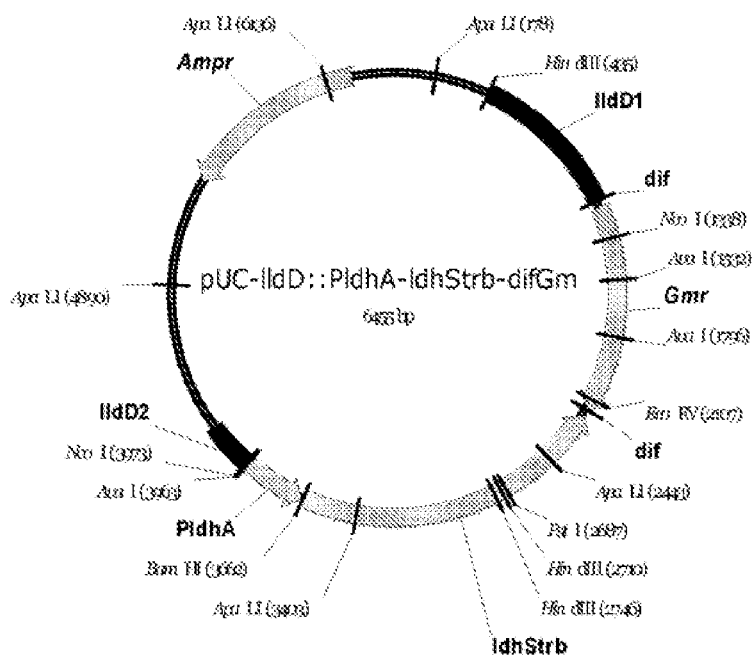
FIG. 13 Physical map of mutant cassette pUC-lldD':: PldhA-ldhStrb-difGm.

A lldD gene segment is obtained by PCR amplification (primers are lldD1 and lldD2), and is introduced to a sub-cloning vector pUC18 to obtain a recombinant plasmid pUC-lldD. A PldhA-ldhStrb-difGm segment is obtained from the recombinant plasmid pUC-PldhA-ldhBcoa-difGm by digestion using BamHI, and is introduced to the BamHI site of the recombinant plasmid pUC-lldD to obtain a recombinant plasmid pUC-lldD::PldhA-ldhStrb-difGm. The physical map of the recombinant plasmid is shown in FIG. 13. The recombinant plasmid pUC-lldD::PldhA-ldhStrb-difGm is digested by SmaI, and a lldD::PldhA-ldhStrb-difGm gene segment is obtained by glue extraction.

Example 14—Construction of Mutant Cassette ldhA: PldhA-ldhLca-difGm

Figure 14:
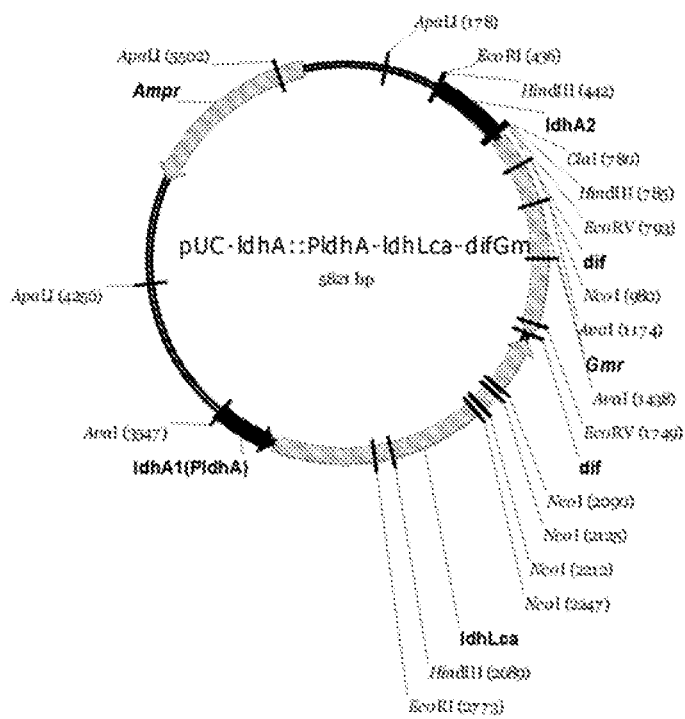
FIG. 14 Physical map of mutant cassette pUC-ldhA':: PldhA-ldhLca-difGm.

The recombinant plasmid pUC-ldhA in example 10 is digested using PstI for removing 400 bps fragments therein, and pfu polymerase is used to make the sticky ends blunt. Then it is ligated to the segment PldhA-ldhLca-difGm obtained by a digestion of the recombinant plasmid pUC-PldhA-ldhLca-difGm in example 12 by BamHI followed by blunting with pfu polymerase, so that a recombinant plasmid pUC-ldhA::PldhA-ldhLca-difGm is obtained. The physical map of the obtained recombinant plasmid is shown in FIG. 14. The recombinant plasmid is digested by ApaLI, and the linearized plasmid is recycled through glue extraction. Then a PCR amplification is carried out using ldhA3 and LDH4 as primers to obtain ldhA::PldhA-ldhLca-difGm gene fragment.

Example 15—Construction of Mutant Cassette ldhA: PldhA-ldhStrb-difGm

Figure 15:
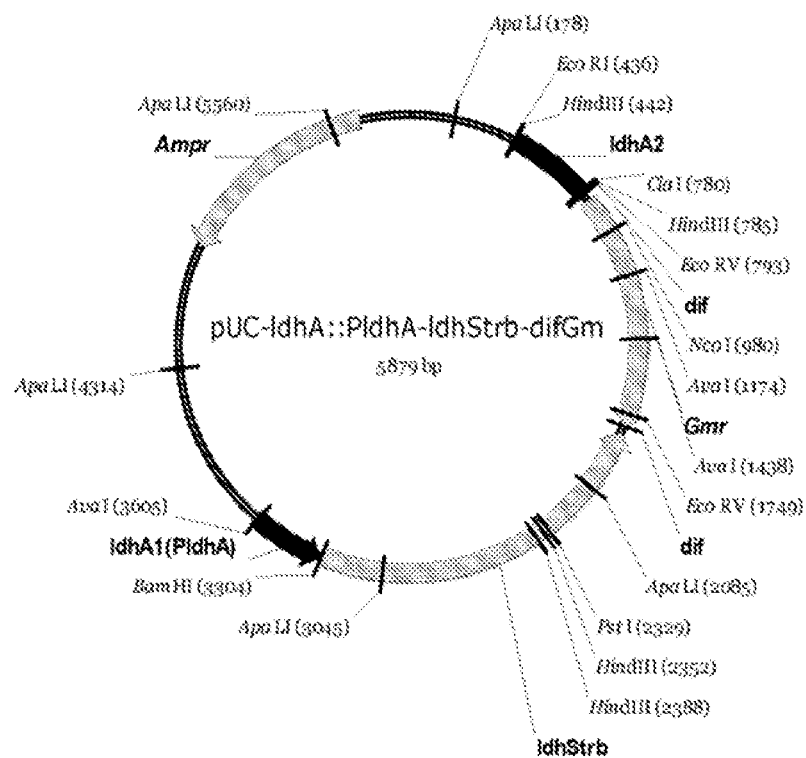
FIG. 15 Physical map of mutant cassette pUC-ldhA':: PldhA-ldhStrb-difGm.

The recombinant plasmid pUC-ldhA in example 10 is digested using PstI for removing 400 bps fragments therein, and the sticky tail end is blunted by a pfu polymerase. Then it is ligated to the segment pldhA-ldhStrb-difGm obtained by a digestion of the recombinant plasmid pUC-PldhA-ldhStrb-difGm in example 13 by BamHI followed by a blunting with pfu polymerase, so that a recombinant plasmid pUC-ldhA:: PldhA-ldhStrb-difGm is obtained. The physical map of the obtained recombinant plasmid is shown in FIG. 15. The recombinant plasmid is digested by ApaLI, and the linearized plasmid is recycled through glue extraction. Then a PCR amplification is carried out using ldhA3 and LDH4 as primers to obtain ldhA::PldhA-ldhStrb-difGm gene fragment.

Example 16—Construction of Mutant Cassette thiE::PldhA-ldhLca-difGm

Figure 16:
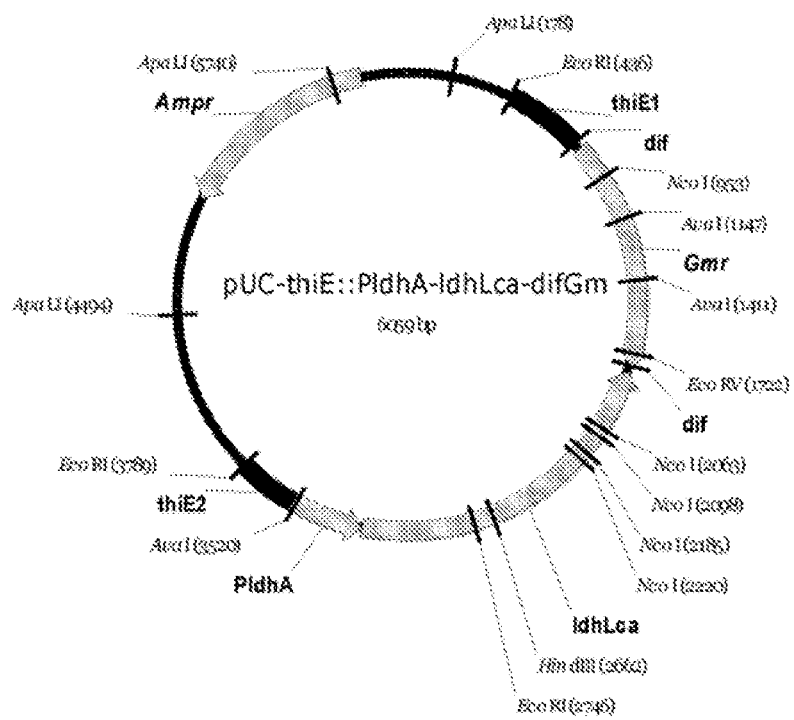
FIG. 16 Physical map of mutant cassette pUC-thiE':: PldhA-ldhLca-difGm.

The recombinant plasmid pUC-PldhA-ldhLca-difGm in example 12 is digested using BamHI to obtain PldhA-ldhLca-difGm segment, and the segment is blunted by DNA polymerase pfu. Then it is introduced to the StuI site of the recombinant plasmid pUC-thiE in example 2 to obtain a recombinant plasmid pUC-thiE::PldhA-ldhLca-difGm. The physical map of the obtained recombinant plasmid is shown in FIG. 16. The recombinant plasmid pUC-thiE::PldhA-ldhLca-difGm is digested by ApaLI, and the linearized plasmid is recycled through glue extraction. Then a PCR amplification is carried out using ThiE1p and ThiE2p as primers to obtain thiE::PldhA-ldhLca-difGm gene fragment.

Example 17—Construction of Mutant Cassette thiE:: PldhA-ldhStrb-difGm

Figure 17:
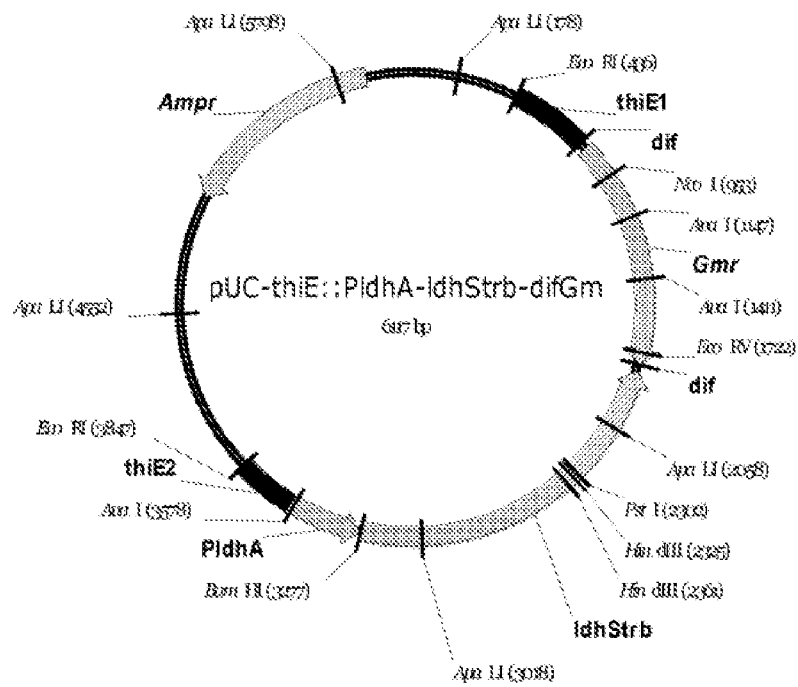
FIG. 17 Physical map of mutant cassette pUC-thiE':: PldhA-ldhStrb-difGm.

The recombinant plasmid pUC-PldhA-ldhStrb-difGm in example 13 is digested using BamHI to obtain PldhA-ldhStrb-difGm segment, and the segment is blunted by DNA polymerase pfu. Then it is introduced to the StuI site of the recombinant plasmid pUC-thiE in example 2 to obtain a recombinant plasmid pUC-thiE::PldhA-ldhStrb-difGm. The physical map of the obtained recombinant plasmid is shown in FIG. 17. The recombinant plasmid pUC-thiE::PldhA-ldhStrb-difGm is digested by ApaLI, and the linearized plasmid is recycled through glue extraction. Then a PCR amplification is carried out using ThiE1p and ThiE2p as primers to obtain thiE::PldhA-ldhStrb-difGm gene fragment.

Example 18—Construction of Mutant Cassette thiE::PldhA-ldhBcoa-difGm

Figure 18:
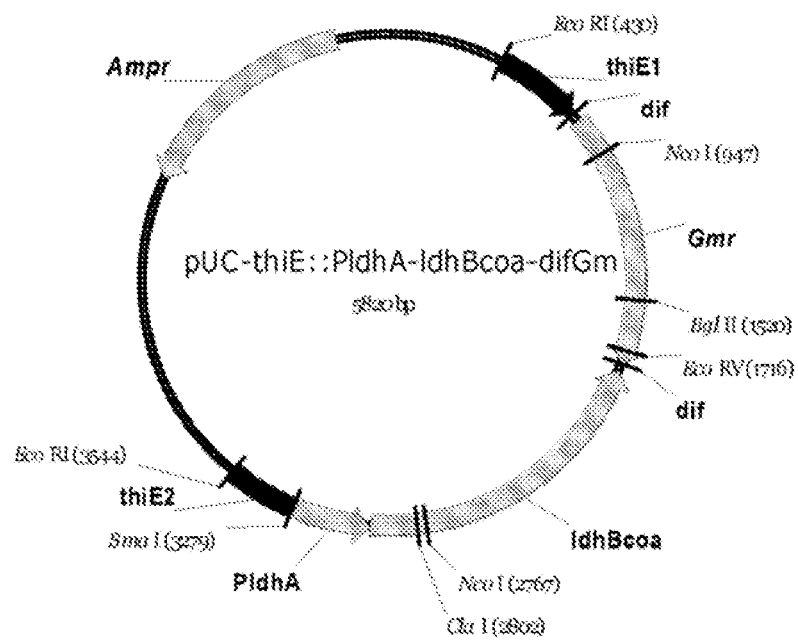
FIG. 18 Physical map of mutant cassette pUC-thiE':: PldhA-ldhBcoa-difGm.

The recombinant plasmid pUC-PldhA-ldhBcoa-difGm in example 11 is digested using BamHI to obtain PldhA-ldhBcoa-difGm segment, and the segment is blunted by DNA polymerase pfu. Then it is introduced to the StuI site of the recombinant plasmid pUC-thiE in example 2 to Obtain a recombinant plasmid pUC-thiE::PldhA-ldhBcoa-difGm. The physical map of the obtained recombinant plasmid is shown in FIG. 18. The recombinant plasmid pUC-thiE::PldhA-ldhBcoa-difGm is digested by ApaLI, and the linearized plasmid is recycled through glue extraction. Then a PCR amplification is carried out using ThiE1p and ThiE2p as primers to obtain thiE::PldhA-ldhBcoa-difGm gene fragment.

Example 19—Construction of Temperature Controllable Type of Extremely High Optical Pure D-lactic Acid Producing Strain Promoter ldhAp of lactic dehydrogenase gene in starting strain B0013 is replaced with promoter pR-pL by means of gene integration technology (Love C. A. et al., Gene, 1996, 176:49-53) to obtain a recombinant sham *E. coli* B0013-010 B (B0013 ldhA::kan-clts857-pR-pL).

Example 20—Construction of Growth—Quantitatively Controllable Type of Extremely High Optical Pure D-lactic Acid Producing Strain A gene integration technology is utilized to construct a thiamine phosphate synthase (thiE) coding gene deletion mutant cassette thiE'::difGm, deleting the thiE gene of the recombinant strain obtained in step 2, and the recombinant strain *E. coli* B0013-020 B (B0013 010B thiE::dif).

Example 21—Construction of D-lactic Acid Metabolism Utilization Pathway Blocking Type of Extremely High Optical Pure D-lactic Acid Producing Strain A gene integration technology is utilized to construct a mutant cassette dld'::difGm used for deleting FAD-dependent type D-lactic dehydrogenase (dld) encoding gene, then the dld gene of the recombinant strain obtained in the step 3 is deleted, thus the recombinant strain *E. coli* B0013-030B (B0013-020B dld::dif) is obtained.

Example 22—Construction of Anaerobic Acetic Acid Synthesis Pathway Blocking Type of Extremely High Optical Pure D-lactic Acid Producing Strain A gene integration technology is utilized to construct a mutant cassette ackA-pta'::difGm used for deleting acetic acetokinase (ackA) and phosphotransacetylase (pta) coding gene, then the ackA-pta gene of the recombinant strain obtained in step 4 is deleted, thus the recombinant strain *E. coli* B0013-040B (B0013-030B ackA-pta::dif) is obtained.

Example 23—Construction of Pyruvic Acid Reflux Pathway Blocking Type of Extremely High Optical Pure D-lactic Acid Producing Strain A gene integration technology is utilized to construct a mutant cassette pps'::difGm used for deleting phosphoenol pyruvate synthase (pps) coding gene, then the pps gene of the recombinant strains obtained in step 4 and step 5 are deleted, and thus the recombinant strain *E. coli* B0013-040C (B0013-030B pps::dif) and B0013-050 B (B0013-040B pps::dif) are obtained.

Example 24—Construction of Formic Acid Anaerobic Synthesis Pathway Blocking Type of Extremely High Optical Pure D-lactic Acid Producing Strain A gene integration technology is utilized to construct a mutant cassette pflB'::difGm used for deleting pyruvate formate-lyase (pflB) coding gene, then the pflB gene of the recombinant strains obtained in step 4, step 5 and step 6 are deleted, and thus the recombinant strain *E. coli* B0013-040D (B0013-030B pflB::dif) B0013-050C(B0013-040B pflB::dif), B0013-050 D (B0013-040C pflB::dif) and B0013-060 B (B0013-050B pflB::dif) are obtained.

Example 25—Construction of Acetic Acid Aerobic Synthesis Pathway Blocking Type of Extremely High Optical Pure D-lactic Acid Producing Strain A gene integration technology is utilized to construct a mutant cassette poxB'::difGm used for deleting pyruvate oxidase (poxB) coding gene, then the poxB gene of the recombinant strains obtained in step 4, step 5, step 6 and step 7 are deleted, and thus the recombinant strain *E. coli* B0013-040E (B0013-030B poxB::dif), B0013-050E (B0013-040B poxB::dif), B0013-050 F(B0013-040C poxB::dif), B0013-060C (B0013-050B poxB::dif), B0013-050G (B0013-040D poxB::dif), B0013-060D (B0013-050C poxB::dif), B0013-060F (B0013-050D poxB::dif), and B0013-070B (B0013-060B poxB::dif) are obtained.

Example 26—Construction of Butanedioic Acid Synthesis Pathway Blocking Type of Extremely High Optical Pure D-lactic Acid Producing Strain A gene integration technology is utilized to construct a mutant cassette frdA'::difGm used for deleting fumaric reductase (frdA) coding gene, then the frdA gene of the recombinant strains obtained in step 4, step 5, step 6, step 7 and step 8 are deleted, and thus the recombinant strain *E.* coli B0013-040F (B0013-030B frdA::dif), B0013-050H (B0013-040B frdA::dif), B0013-050I (B0013-040C frdA::dif), B0013-060G (B0013-050B frdA::dif), B0013-050J (B0013-040D frdA::dif), B0013-060H (B0013-050C frdA::dif), B0013-060I (B0013-050D frdA::dif), B0013-070C (B0013-060B frdA::dif), B0013-050K (B0013-040E frdA::dif), B0013-060J (B0013-050E frdA::dif), B0013-060K (B0013-050F frdA::dif), B0013-070D (B0013-060C frdA::dif), B0013-060L (B0013-050G frdA::dif), B0013-070E (B0013-060D frdA::dif), B0013-070F (B0013-060F frdA::dif) and B0013-080B (B0013-070B frdA::dif) are obtained.

Example 27—Construction of Ethanol Synthesis Pathway Blocking Type of Extremely High Optical Pure D-lactic Acid Producing Strain A gene integration technology is utilized to construct a mutant cassette adhE':: difGm used for deleting ethanol dehydrogenase (adhE) coding gene, then the adhE gene of the recombinant strains obtained in step 4, step 5, step 6, step 7, step 8 and step 9 are deleted, and thus the recombinant strain E. coli B0013-040G (B0013-030B adhE::dif), B0013-050L (B0013-040B adhE::dif), B0013-050M (B0013-040C adhE::dif), B0013-060M (B0013-050B adhE::dif), B0013-050N (B0013-040D adhE::dif), B0013-060N (B0013-050C adhE::dif), B0013-060O (B0013-050D adhE::dif), B0013-070G (B0013-060B adhE::dif), B0013-050O (B0013-040E adhE::dif), B0013-060P (B0013-050E adhE::dif), B0013-060Q (B0013-050F adhE::dif), B0013-070H (B0013-060C adhE::dif), B0013-060R (B0013-050G adhE::dif), B0013-070I (B0013-060D adhE::dif), B0013-070J (B0013-060F adhE::dif), B0013-080C (B0013-070B adhE::dif), B0013-050P (B0013-040F adhE::dif), B0013-060S (B0013-050H adhE::dif), B0013-060T (B0013-050I adhE::dif), B0013-070K (B0013-060G adhE::dif), B0013-060U (B0013-050J adhE::dif), B0013-070L (B0013-060H adhE::dif), B0013-070M (B0013-060I adhE::dif), B0013-080D (B0013-070C adhE::dif), B0013-060V (B0013-050K adhE::dif), B0013-070N (B0013-060J adhE::dif), B0013-070O (B0013-060K frdA::dif), B0013-080E (B0013-070D adhE::dif), B0013-070P (B0013-060L adhE::dif), B0013-080F (B0013-070E adhE::dif), B0013-080G (B0013-070F adhE::dif) and B0013-090B (B0013-080B adhE::dif) are obtained.

Example 28—Construction of D-lactic Acid Synthesis Pathway Blocking Type of Strain A gene integration technology is utilized to construct a mutant cassette ldhA':: difGm used for deleting D-lactate dehydrogenase (ldhA) coding gene, then the ldhA gene of the recombinant strains B0013-070 is deleted, and thus the recombinant strain E. coli B0013-080H (B0013-070 ldhA::dif) is obtained.

Example 29—Construction of D-lactic Acid Synthesis Pathway Blocking Type Extremely High Optical Purity D-lactic Acid Producing Strain A gene integration technology is utilized to construct a mutant cassette ldhA':: PldhA-ldhLca-difGm used for deleting D-lactate dehydrogenase (ldhA) coding gene, then the ldhA gene of the recombinant bacterium B0013-070 is deleted, and thus the recombinant strain E. coli B0013-080I (B0013-070 ldhA::PldhA-ldhLca-dif) is obtained.

Example 30—Construction of D-lactic Acid Synthesis Pathway Blocking Type of Extremely High Optical Pure L-lactic Acid Producing Strain A gene integration technology is utilized to construct a mutant cassette ldhA':: PldhA-ldhStrb-difGm used for deleting D-lactate dehydrogenase (ldhA) coding gene, then the ldhA gene of the recombinant strain B0013-070 is deleted, and thus the recombinant strain E. coli B0013-080J (B0013-070 ldhA::PldhA-ldhStrb-dif) is obtained.

Example 31—Construction of L-lactic Acid Metabolism Utilization Pathway Blocking Type of Extremely High Optical Pure L-lactic Acid Producing Strain A gene integration technology is utilized to construct a mutant cassette lldD':: PldhA-ldhBcoa-difGm used for deleting D-lactic dehydrogenase gene (lldD) coding gene, then the lldD gene of the recombinant strain B0013-070, B0013-080H, B0013-080I and B0013-080J are deleted, and thus the recombinant strains E. coli B0013-080K (B0013-070 lldD::PldhA-ldhBcoa-dif), B0013-090C (B0013-080H lldD::PldhA-ldhBcoa-dif), B0013-090D (B0013-080I lldD:: PldhA-ldhBcoa-dif) and B0013-090E (B0013-080J lldD:: PldhA-ldhBcoa-dif) are obtained.

Example 32—Construction of L-lactic Acid Metabolism Utilization Pathway Blocking Type of Extremely High Optical Pure L-lactic Acid Producing Strain A gene integration technology is utilized to construct a mutant cassette lldD':: PldhA-ldhLca-difGm used for deleting the coding gene of L-lactic dehydrogenase gene (lldD) adopted FMN as coenzyme, then the lldD gene of the recombinant strains B0013-070, B0013-080H, B0013-080I and B0013-080J are deleted, and thus the recombinant strain E. coli B0013-080L (B0013-070 lldD::PldhA-ldhLca-dif), B0013-090F (B0013-080H lldD::PldhA-ldhLca-dif), B0013-090G (B0013-080I lldD:: PldhA-ldhLca-dif) and B0013-090H (B0013-080J lldD:: PldhA-ldhLca-dif) are obtained.

Example 33—Construction of L-lactic Acid Metabolism Utilization Pathway Blocking Type Extremely High Optical Pure L-lactic Acid Producing Strain A gene integration technology is utilized to construct a mutant cassette lldD':: PldhA-ldhLca-difGm used for deleting the coding gene of L-lactic dehydrogenase gene (lldD) in which FMN is taken as coenzyme, then the lldD gene of the recombinant strains B0013-070, B0013-080H, B0013-080I and B0013-080J are deleted, and thus the recombinant strain E. coli B0013-080M (B0013-070 lldD:: PldhA-ldhStrb-dif), B0013-090I (B0013-080H lldD:: PldhA-ldhStrb-dif), B0013-090J (B0013-080I lldD:: PldhA-ldhStrb-dif) and B0013-090K (B0013-080J lldD:: PldhA-ldhStrb-dif) are obtained.

Example 34—Construction of Growth—Quantitatively Controllable Type of Extremely High Optical Pure L-lactic Acid Producing Strain A gene integration technology is utilized to construct a mutant cassette thiE'::difGm used for deleting the coding gene of thiamine phosphate synthase (thiE), then the thiE gene of the recombinant strains in step 11, step 12, step 13, step 14, step 15 and step 16 are deleted, and thus the recombinant strains *E. coli* B0013-090L (B0013-080H thiE::dif), B0013-090M (B0013-080I thiE::dif), B0013-090N (B0013-080J thiE::dif), B0013-090O (B0013-080K thiE::dif), B0013-100B (B0013-090C thiE::dif), B0013-100C (B0013-090D thiE::dif), B0013-100D (B0013-090E thiE::dif), B0013-090E (B0013-080L thiE::dif), B0013-100E (B0013-090F thiE::dif), B0013-100F (B0013-090G thiE::dif), B0013-100G (B0013-090H thiE::dif), B0013-080N (B0013-070 thiE::dif), B0013-100H (B0013-090I thiE::dif), B0013-100I (B0013-090J thiE::dif) and B0013-100J (B0013-090K thiE::dif) are obtained.

Example 35—Construction of Growth—Quantitatively Controllable Type of Extremely High Optical Pure L-lactic Acid Producing Strain A gene integration technology is utilized to construct a mutant cassette thiE'::PldhA-ldhLca-difGm used for deleting the coding gene of thiamine phosphate synthase (thiE), then the thiE gene of the recombinant strains in step 11, step 12, step 13, step 14, step 15 and step 16 are deleted, and thus the recombinant strains *E. coli* B0013-090P (B0013-080H thiE::PldhA-ldhLca-dif), B0013-090Q (B0013-080I thiE::PldhA-ldhLca-dif), B0013-090R (B0013-080J thiE::PldhA-ldhLca-dif), B0013-090S (B0013-080K thiE::PldhA-ldhLca-dif), B0013-100K (B0013-090C thiE::PldhA-ldhLca-dif), B0013-100L (B0013-090D thiE::PldhA-ldhLca-dif), B0013-100M (B0013-090E thiE::PldhA-ldhLca-dif), B0013-090T (B0013-080L thiE::PldhA-ldhLca-dif), B0013-100N (B0013-090F thiE::PldhA-ldhLca-dif), B0013-100O (B0013-090G thiE::PldhA-ldhLca-dif), B0013-100P (B0013-090H thiE::PldhA-ldhLca-dif) B0013-080O (B0013-070 thiE::PldhA-ldhLca-dif), B0013-100Q (B0013-090I thiE::PldhA-ldhLca-dif), B0013-100R (B0013-090J thiE::PldhA-ldhLca-dif) and B0013-100S (B0013-090K thiE::PldhA-ldhLca-dif) are obtained.

Example 36—Construction of Growth—Quantitatively Controllable Type of Extremely-High Optical Pure L-lactic Acid Producing Strain A gene integration technology is utilized to construct a mutant cassette thiE'::PldhA-ldhStrb-difGm used for deleting the coding gene of thiamine phosphate synthase (thiE), then the thiE gene of the recombinant strains in step 11, step 12, step 13, step 14, step 15 and step 16 are deleted, and thus the recombinant strains *E. coli* B0013-090U (B0013-080H thiE::PldhA-ldhStrb-dif), B0013-090V (B0013-080I thiE::PldhA-ldhStrb-dif), B0013-090W (B0013-080J thiE::PldhA-ldhStrb-dif), B0013-090X (B0013-080K thiE::PldhA-ldhStrb-dif), B0013-100T (B0013-090C thiE::PldhA-ldhStrb-dif), B0013-100U (B0013-090D thiE::PldhA-ldhStrb-dif), B0013-100V (B0013-090E thiE::PldhA-ldhStrb-dif), B0013-090Y (B0013-080L thiE::PldhA-ldhStrb-dif), B0013-100W (B0013-090F thiE::PldhA-ldhStrb-dif), B0013-100X (B0013-090G thiE::PldhA-ldhStrb-dif), B0013-100Y (B0013-090H thiE::PldhA-ldhStrb-dif), B0013-080P (B0013-070 thiE::PldhA-ldhStrb-dif), B0013-100Z (B0013-090I thiE::PldhA-ldhStrb-dif), B0013-100BB (B0013-090J thiE::PldhA-ldhStrb-dif) and B0013-100BC (B0013-090K thiE::PldhA-ldhStrb-dif) are obtained.

Example 37—Construction of Growth—Quantitatively Controllable Type of Extremely High Optical Pure L-lactic Acid Producing Strain A gene integration technology is utilized to construct a mutant cassette thiE'::PldhA-ldhBcoa-difGm used for deleting the coding gene of thiamine phosphate synthase (thiE), then the thiE gene of the recombinant strains in step 11, step 12, step 13, step 14, step 15 and step 16 are deleted, and thus the recombinant strains *E. coli* B0013-090Z (B0013-080H thiE::PldhA-ldhBcoa-dif), B0013-090BB (B0013-080I thiE::PldhA-ldhBcoa-dif), B0013-090BC (B0013-080J thiE::PldhA-ldhBcoa-dif), B0013-090BD (B0013-080K thiE::PldhA-ldhBcoa-dif), B0013-100BD (B0013-090C thiE::PldhA-ldhBcoa-dif), B0013-100BE (B0013-090D thiE::PldhA-ldhBcoa-dif), B0013-100BF (B0013-090E thiE::PldhA-ldhBcoa-dif), B0013-090BE (B0013-080L thiE::PldhA-ldhBcoa-dif), B0013-100BG (B0013-090F thiE::PldhA-ldhBcoa-dif), B0013-100BH (B0013-090G thiE::PldhA-ldhBcoa-dif), B0013-100BI (B0013-090H thiE::PldhA-ldhBcoa-dif), B0013-080Q (B0013-070 thiE::PldhA-ldhBcoa-dif), B0013-100BJ (B0013-090I thiE::PldhA-ldhBcoa-dif), B0013-100BK (B0013-090J thiE::PldhA-ldhBcoa-dif), B0013-100BL (B0013-090K thiE::PldhA-ldhBcoa-dif), B0013-100BM (B0013-090U thiE::PldhA-ldhBcoa-dif), B0013-100BN (B0013-090V thiE::PldhA-ldhBcoa-dif), B0013-100BO (B0013-090W thiE::PldhA-ldhBcoa-dif), B0013-100BP (B0013-090X thiE::PldhA-ldhBcoa-dif), B0013-101B (B0013-100T thiE::PldhA-ldhBcoa-dif), B0013-101C (B0013-100U thiE::PldhA-ldhBcoa-dif), B0013-101D (B0013-100V thiE::PldhA-ldhBcoa-dif), B0013-100BQ (B0013-090Y thiE::PldhA-ldhBcoa-dif), B0013-101E (B0013-100W thiE::PldhA-ldhBcoa-dif), B0013-101F (B0013-100X thiE::PldhA-ldhBcoa-dif), B0013-101G (B0013-100Y thiE::PldhA-ldhBcoa-dif), B0013-090BF (B0013-080P thiE::PldhA-ldhBcoa-dif), B0013-101H (B0013-100Z thiE::PldhA-ldhBcoa-dif), B0013-101I (B0013-100BB thiE::PldhA-ldhBcoa-dif) and B0013-101J (B0013-100BC thiE::PldhA-ldhBcoa-dif) are obtained.

Figure 19:
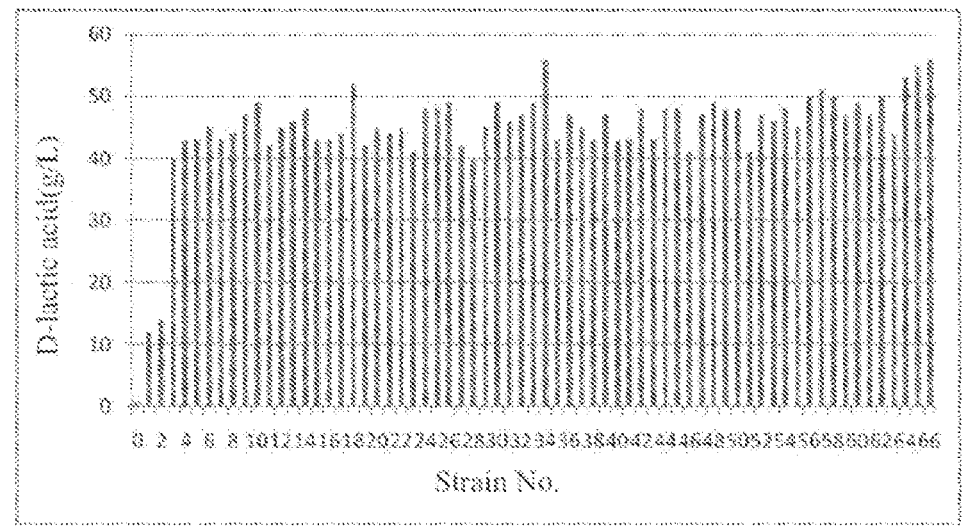
FIG. 19 Screening result of the extremely high optical pure D-lactic acid producing strain.

Example 38—Screening of D-lactic Acid High-Yield Strain with Extremely High Optical Purity The recombinant strains obtained in the steps 19-27 are aerobically cultured respectively at 25-36° C., 200 r/min for 6-10 h with 0.06-100 μg/L thiamine firstly, then the lactic acid fermentation is carried out by stationary culture at 37-50° C. Adopting the starting strain B0013-070 as a control, the synthesis level of D-lactic acid, the optical purity and the chemical purity of the produced D-lactic acid are analyzed, to screen out the optimal strain. The screening result is shown in FIG. 19 and table 1.

TABLE 1 screening result of D-lactic acid high-yield strain with extremely high optical purity

| Strain No. | Strain Numbering | Yield (%, w/v) | optical purity (%, w/w) | chemical purity (%, w/w) |
|---|---|---|---|---|
| 0 | B0013-070 | 0.6 | 99.9 | 75 |
| 1 | B0013-010B | 12 | 99.95 | 79 |
| 2 | B0013-020B | 14 | 99.96 | 80 |
| 3 | B0013-030B | 40 | 99.95 | 85 |

TABLE 1-continued screening result of D-lactic acid high-yield strain with extremely high optical purity

| Strain No. | Strain Numbering | Yield (%, w/v) | optical purity (%, w/w) | chemical purity (%, w/w) |
|---|---|---|---|---|
| 4 | B0013-040B | 43 | 99.97 | 88 |
| 5 | B0013-040C | 43 | 99.96 | 85 |
| 6 | B0013-050B | 45 | 99.97 | 90 |
| 7 | B0013-040D | 43 | 99.95 | 90 |
| 8 | B0013-050C | 44 | 99.96 | 89 |
| 9 | B0013-050D | 47 | 99.95 | 89 |
| 10 | B0013-060B | 49 | 99.97 | 92 |
| 11 | B0013-040E | 42 | 99.96 | 78 |
| 12 | B0013-050E | 45 | 99.97 | 87 |
| 13 | B0013-050F | 46 | 99.97 | 88 |
| 14 | B0013-060C | 48 | 99.96 | 90 |
| 15 | B0013-050G | 43 | 99.97 | 86 |
| 16 | B0013-060D | 43 | 99.97 | 90 |
| 17 | B0013-060F | 44 | 99.95 | 89 |
| 18 | B0013-070B | 52 | 99.96 | 94 |
| 19 | B0013-040F | 42 | 99.95 | 87 |
| 20 | B0013-050H | 45 | 99.97 | 90 |
| 21 | B0013-050I | 44 | 99.96 | 85 |
| 22 | B0013-060G | 45 | 99.97 | 86 |
| 23 | B0013-050J | 41 | 99.97 | 87 |
| 24 | B0013-060H | 48 | 99.95 | 90 |
| 25 | B0013-060I | 48 | 99.96 | 91 |
| 26 | B0013-070C | 49 | 99.95 | 88 |
| 27 | B0013-050K | 42 | 99.97 | 85 |
| 28 | B0013-060J | 40 | 99.95 | 78 |
| 29 | B0013-060K | 45 | 99.96 | 89 |
| 30 | B0013-070D | 49 | 99.95 | 90 |
| 31 | B0013-060L | 46 | 99.97 | 88 |
| 32 | B0013-070E | 47 | 99.96 | 81 |
| 33 | B0013-070F | 49 | 99.97 | 89 |
| 34 | B0013-080B | 56 | 99.95 | 94 |
| 35 | B0013-040G | 43 | 99.96 | 79 |
| 36 | B0013-050L | 47 | 99.95 | 86 |
| 37 | B0013-050M | 45 | 99.95 | 88 |
| 38 | B0013-060M | 43 | 99.96 | 90 |
| 39 | B0013-050N | 47 | 99.95 | 87 |
| 40 | B0013-060N | 43 | 99.97 | 80 |
| 41 | B0013-060O | 43 | 99.96 | 83 |
| 42 | B0013-070G | 48 | 99.95 | 89 |
| 43 | B0013-050O | 43 | 99.96 | 77 |
| 44 | B0013-060P | 48 | 99.95 | 91 |
| 45 | B0013-060Q | 48 | 99.95 | 90 |
| 46 | B0013-070H | 41 | 99.96 | 93 |
| 47 | B0013-060R | 47 | 99.95 | 88 |
| 48 | B0013-070I | 49 | 99.97 | 90 |
| 49 | B0013-070J | 48 | 99.95 | 89 |
| 50 | B0013-080C | 48 | 99.96 | 92 |
| 51 | B0013-050P | 41 | 99.95 | 86 |
| 52 | B0013-060S | 47 | 99.95 | 88 |
| 53 | B0013-060T | 46 | 99.95 | 87 |
| 54 | B0013-070K | 48 | 99.96 | 90 |
| 55 | B0013-060U | 45 | 99.95 | 88 |
| 56 | B0013-070L | 50 | 99.95 | 92 |
| 57 | B0013-070M | 51 | 99.96 | 92 |
| 58 | B0013-080D | 50 | 99.95 | 94 |
| 59 | B0013-060V | 47 | 99.96 | 89 |
| 60 | B0013-070N | 49 | 99.95 | 90 |
| 61 | B0013-070O | 47 | 99.95 | 88 |
| 62 | B0013-080E | 50 | 99.96 | 86 |
| 63 | B0013-070P | 44 | 99.95 | 90 |
| 64 | B0013-080F | 53 | 99.97 | 93 |
| 65 | B0013-080G | 55 | 99.95 | 95 |
| 66 | B0013-090B | 56 | 99.96 | 97 |

Figure 20:
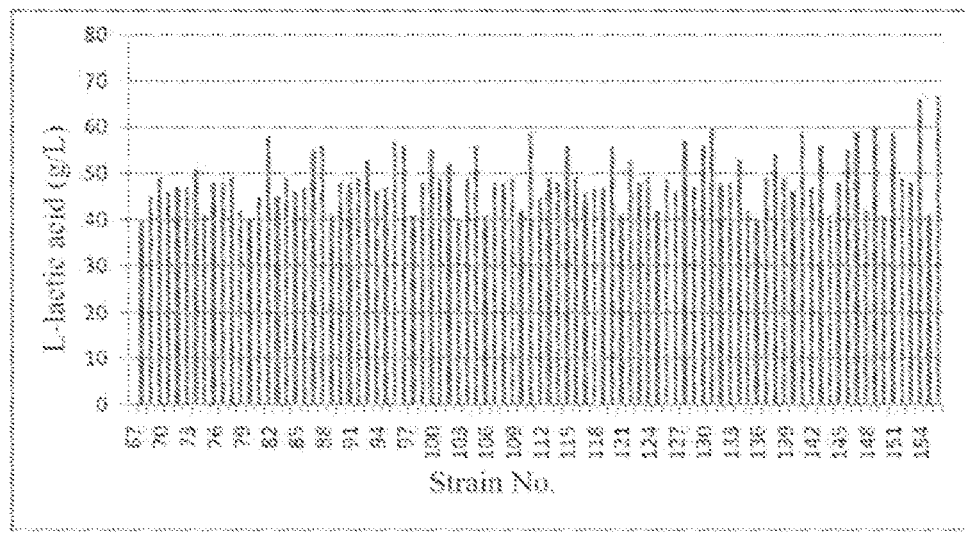
FIG. 20 Screening result of the extremely high optical pure L-lactic acid producing strain.

Example 39—Screening of L-lactic Acid High-Yield Strain with Extremely High Optical Purity The recombinant strains obtained in the steps 28-37 are aerobically cultured respectively at 25-36° C., and 200 r/min for 6-10 h with 0.06-100 μg/L thiamine firstly, then the lactic acid fermentation is carried out by stationary culture at 37-50° C. Adopting the starting strain B0013-070 as a control, the synthesis level of L-lactic acid, the optical purity and the chemical purity of the producted L-lactic acid are analyzed, to screen out the optimal strain. The screening result is shown in FIG. 20 and table 2.

TABLE 2

Screening result of extremely high optical pure L-lactic acid strain with high-yield

| Strain No. | Strain Numbering | Yield (%, w/v) | optical purity (%, w/w) | chemical purity (%, w/w) |
|---|---|---|---|---|
| 0 | B0013-070 | 0 | 0 | 0 |
| 67 | B0013-080H | 0 | 0 | 0 |
| 68 | B0013-080I | 40 | 99.96 | 88 |
| 69 | B0013-080J | 45 | 99.97 | 85 |
| 70 | B0013-080K | 49 | 99.96 | 88 |
| 71 | B0013-090C | 46 | 99.96 | 85 |
| 72 | B0013-090D | 47 | 99.95 | 90 |
| 73 | B0013-090E | 47 | 99.96 | 90 |
| 74 | B0013-080L | 51 | 99.97 | 89 |
| 75 | B0013-090F | 41 | 99.96 | 97 |
| 76 | B0013-090G | 48 | 99.95 | 92 |
| 77 | B0013-090H | 48 | 99.97 | 96 |
| 78 | B0013-080M | 49 | 99.96 | 87 |
| 79 | B0013-090I | 42 | 99.95 | 88 |
| 80 | B0013-090J | 40 | 99.96 | 86 |
| 81 | B0013-090K | 45 | 99.97 | 92 |
| 82 | B0013-090L | 58 | 99.97 | 98 |
| 83 | B0013-090M | 45 | 99.95 | 89 |
| 84 | B0013-090N | 49 | 99.96 | 94 |
| 85 | B0013-090O | 46 | 99.97 | 87 |
| 86 | B0013-100B | 47 | 99.95 | 90 |
| 87 | B0013-100C | 55 | 99.96 | 93 |
| 88 | B0013-100D | 56 | 99.97 | 86 |
| 89 | B0013-090E | 41 | 99.97 | 87 |
| 90 | B0013-100E | 48 | 99.95 | 95 |
| 91 | B0013-100F | 48 | 99.96 | 91 |
| 92 | B0013-100G | 49 | 99.95 | 88 |
| 93 | B0013-080N | 53 | 99.95 | 93 |
| 94 | B0013-100H | 46 | 99.97 | 89 |
| 95 | B0013-100I | 47 | 99.96 | 89 |
| 96 | B0013-100J | 57 | 99.95 | 90 |
| 97 | B0013-090P | 56 | 99.95 | 88 |
| 98 | B0013-090Q | 41 | 99.95 | 81 |
| 99 | B0013-090R | 48 | 99.97 | 89 |
| 100 | B0013-090S | 55 | 99.97 | 92 |
| 101 | B0013-100K | 49 | 99.96 | 97 |
| 102 | B0013-100L | 52 | 99.95 | 86 |
| 103 | B0013-100M | 40 | 99.95 | 88 |
| 104 | B0013-090T | 49 | 99.96 | 90 |
| 105 | B0013-100N | 56 | 99.95 | 87 |
| 106 | B0013-100O | 41 | 99.97 | 80 |
| 107 | B0013-100P | 48 | 99.96 | 83 |
| 108 | B0013-080O | 48 | 99.96 | 89 |
| 109 | B0013-100Q | 49 | 99.96 | 77 |
| 110 | B0013-100R | 42 | 99.95 | 91 |
| 111 | B0013-100S | 59 | 99.95 | 88 |
| 112 | B0013-090U | 45 | 99.97 | 93 |
| 113 | B0013-090V | 49 | 99.95 | 88 |
| 114 | B0013-090W | 48 | 99.97 | 93 |
| 115 | B0013-090X | 56 | 99.95 | 89 |
| 116 | B0013-100T | 49 | 99.95 | 92 |
| 117 | B0013-100U | 46 | 99.95 | 88 |
| 118 | B0013-100V | 47 | 99.95 | 88 |
| 119 | B0013-090Y | 47 | 99.95 | 87 |
| 120 | B0013-100W | 56 | 99.96 | 90 |
| 121 | B0013-100X | 41 | 99.95 | 88 |
| 122 | B0013-100Y | 53 | 99.96 | 92 |
| 123 | B0013-080P | 48 | 99.95 | 92 |
| 124 | B0013-100Z | 49 | 99.95 | 94 |
| 125 | B0013-100BB | 42 | 99.96 | 89 |
| 126 | B0013-100BC | 49 | 99.96 | 90 |
| 127 | B0013-090Z | 46 | 99.95 | 88 |
| 128 | B0013-090BB | 57 | 99.96 | 86 |
| 129 | B0013-090BC | 47 | 99.95 | 90 |
| 130 | B0013-090BD | 56 | 99.97 | 93 |
| 131 | B0013-100BD | 60 | 99.95 | 95 |
| 132 | B0013-100BE | 48 | 99.97 | 97 |

TABLE 2-continued

Screening result of extremely high optical
pure L-lactic acid strain with high-yield

| Strain No. | Strain Numbering | Yield (%, w/v) | optical purity (%, w/w) | chemical purity (%, w/w) |
|---|---|---|---|---|
| 133 | B0013-100BF | 48 | 99.96 | 89 |
| 134 | B0013-090BE | 53 | 99.95 | 90 |
| 135 | B0013-100BG | 42 | 99.97 | 88 |
| 136 | B0013-100BH | 40 | 99.96 | 81 |
| 137 | B0013-100BI | 49 | 99.97 | 89 |
| 138 | B0013-080Q | 54 | 99.95 | 94 |
| 139 | B0013-100BJ | 49 | 99.96 | 79 |
| 140 | B0013-100BK | 46 | 99.95 | 86 |
| 141 | B0013-100BL | 59 | 99.95 | 88 |
| 142 | B0013-100BM | 47 | 99.96 | 90 |
| 143 | B0013-100BN | 56 | 99.95 | 87 |
| 144 | B0013-100BO | 41 | 99.97 | 80 |
| 145 | B0013-100BP | 48 | 99.95 | 83 |
| 146 | B0013-101B | 55 | 99.95 | 89 |
| 147 | B0013-101C | 59 | 99.96 | 77 |
| 148 | B0013-101D | 42 | 99.95 | 91 |
| 149 | B0013-100BQ | 60 | 99.95 | 90 |
| 150 | B0013-101E | 41 | 99.97 | 93 |
| 151 | B0013-101F | 59 | 99.96 | 88 |
| 152 | B0013-101G | 49 | 99.97 | 90 |
| 153 | B0013-090BF | 48 | 99.95 | 89 |
| 154 | B0013-101H | 66 | 99.96 | 92 |
| 155 | B0013-101I | 41 | 99.95 | 86 |
| 156 | B0013-101J | 67 | 99.95 | 98 |

Example 40—Fermentation of Extremely High Optical Pure D-lactic Acid

The optimal strain obtained by example 38 is subjected to a lactic acid fermentation test in a 7 L-30,000 L fermentation tank. During the fermentation process, samples are sampled regularly, and the cell density, the sugar consumption, the lactic acid yield, the metabolic main intermediate product and other organic acid products are analyzed. An aerobic culture at 25-30℃ is carried out until $OD_{600}$ value is about 15-40; and the temperature of the fermentation tank is set to be 37-50℃ to continue the aerobic culture for 0-120 min, and then the ventilation quantity is set to be 0-0.2 vvm to carry out a limited oxygen fermentation, in which the fermentation temperature ranges from 33-39℃ during 0-3 h, 37-42℃ during 3-6 h, 38-45℃ during 6-10 h, 40-48℃ during 10-16 h, and 45-50℃ during 16-24 h; and the fermentation medium is (g/L): diammonium hydrogen phosphate 0-25, monopotassium phosphate 0-5, disodium hydrogen phosphate 0-25, sodium chloride 0-5, $MgSO_4$ 0-0.5, $FeSO_4$ 0-1, $FeCl_3$ 0-1, $CoCl_2$ 0-1, $CuCl_2$ 0-1, $Na_2MoO_4$ 0-1, $H_3BO_3$ 0-1, $MnCl_2$ 0-1, citric acid 0-25, thiamine 0-1, xylose 0-50, glycerol 0-50, glucose 0-50, sulfuric acid 0-5, and pH 6.0-7.5.

Figure 21:
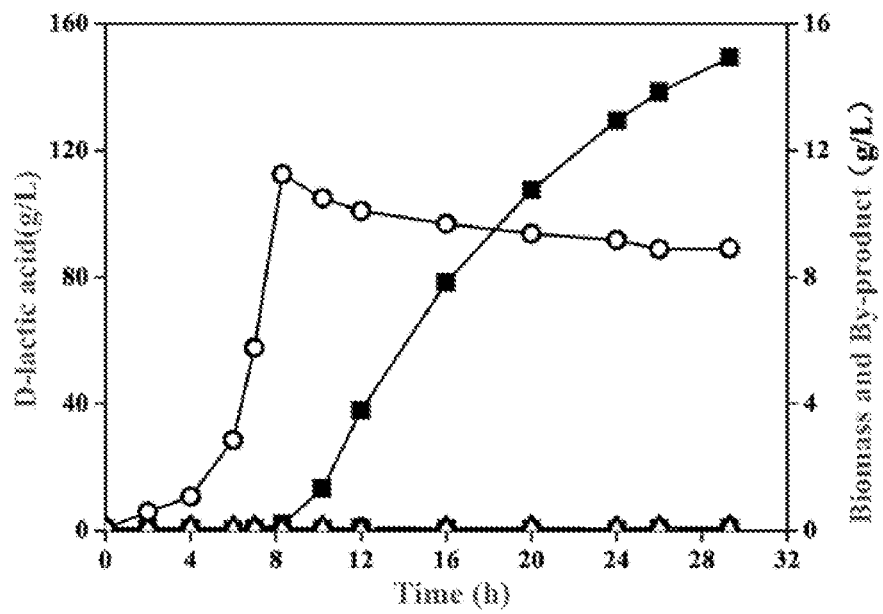
FIG. 21 Producing process of the extremely high optical pure D-lactic acid.
Figure 22:
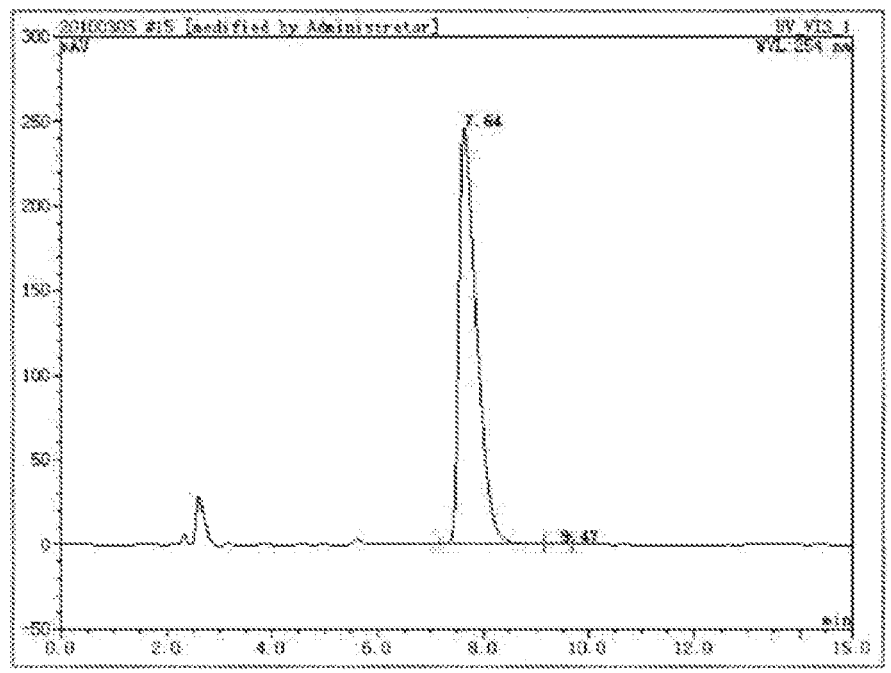
FIG. 22 Optical purity detection spectrum of D-lactic acid.

Detailed fermentation results are shown in FIG. 21 and FIG. 22.

Example 41—Fermentation Production of L-lactic Acid High-Yield Strain with Extremely High Optical Purity The optimal strain obtained by example 39 is subjected to a lactic acid fermentation test in a 7 L-30,000 L fermentation tank. During the fermentation process, samples are sampled regularly, and the cell density, the sugar consumption, the lactic acid yield, the metabolic main intermediate product and other organic acid products are analyzed. An aerobic culture at 25-36℃ is carried out until $OD_{600}$ value is about 15-40; and the temperature of the fermentation tank is set to be 37-50℃ to continue the aerobic culture for 0-120 min, and then the ventilation quantity is set to be 0-0.2 vvm to carry out a limited oxygen fermentation, in which the fermentation temperature ranges from 37-50℃; and the fermentation medium is (g/L): diammonium hydrogen phosphate 0-25, monopotassium phosphate 0-5, disodium hydrogen phosphate 0-25, sodium chloride 0-5, $MgSO_4$ 0-0.5, $FeSO_4$ 0-1, $FeCl_3$ 0-1, $CoCl_2$ 0-1, $CuCl_2$ 0-1, $ZnCl_2$ 0-1, $Na_2MoO_4$ 0-1, $H_3BO_3$ 0-1, $MnCl_2$ 0-1, citric acid 0-25, thiamine 0-1, xylose 0-50, glycerol 0-50, glucose 0-50, sulfuric acid 0-5, and pH 6.0-7.5.

Figure 23:
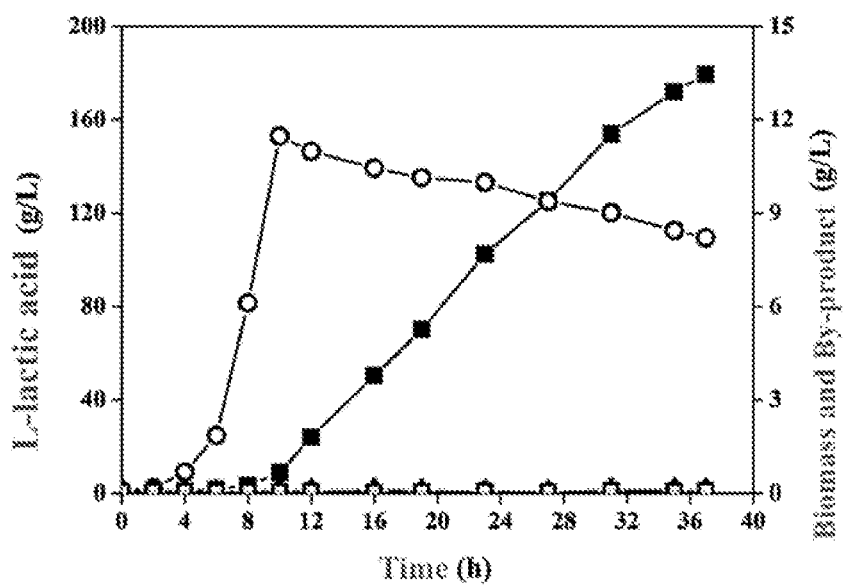
FIG. 23 Producing process of the extremely high optical pure L-lactic.
Figure 24:
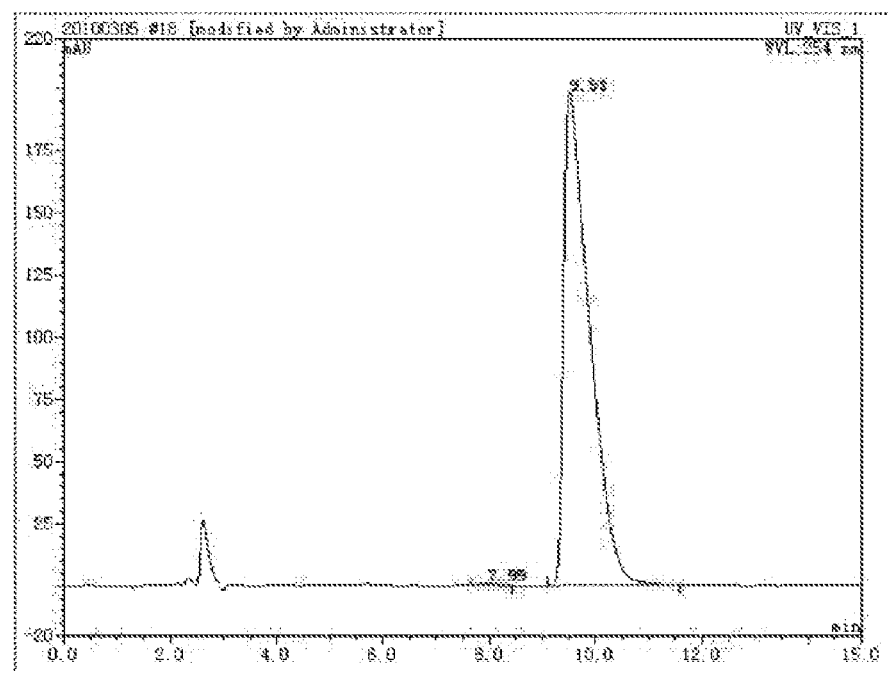
FIG. 24 Optical purity detection spectrum of L-lactic acid.

Detailed fermentation results are shown in FIG. 23 and FIG. 24.

Example 42—Fermentation of Strain to Product Extremely High Optical Pure D-lactic Acid by Five-Batch Fermentation in 10-Ton Tank The optimal strain of producing extremely high pure D-lactic acid obtained by example 38 is subjected to a fermentation in a 10-ton fermentation tank for five batches.

(1) Primary Seed Culture 1 mL strain preserved in an ultra low-temperature glycerol tube was taken and inoculated into to 5 L shake flask with 1 L dedicated liquid medium (ZT1 medium), and cultured at 37℃, 200 r/min for 10-13 h.

Preparation of ZT1 Medium

Components 1, total of 12.6 g, is dissolved by water to 700 mL, and is subjected to sterilization at 121℃ for 20 min.

Components 2, total of 18 g, is dissolved by water to 150 mL, and is subjected to a separate sterilization, and added when inoculating.

Components 3, total of 5 g, is dissolved by water to 150 mL, and is subjected to a separate sterilization, and added when inoculating.

In which the ZT1 medium comprises (g/L): diammonium hydrogen phosphate 0-25, monopotassium phosphate 0-5, disodium hydrogen phosphate 0-25, sodium chloride 0-5, $MgSO_4$ 0-0.5, $FeSO_4$ 0-1, $FeCl_3$ 0-1, $CoCl_2$ 0-1,$CuCl_2$ 0-1, $ZnCl_2$ 0-1, $Na_2MoO_4$ 0-1, $H_3BO_3$ 0-1, $MnCl_2$ 0-1, citric acid 0-25, thiamine 0-1, xylose 0-50, glycerol 0-50, glucose 0-50, sulfuric acid 0-5, and pH 6.0-7.5.

(2) Secondary Seed Culture

The above seed fermentation broth of 1 L is inoculated into a 100 L secondary seed tank with a loading volume of 50 L, and then cultured at 33-37℃, low-ventilation for 10-13 h.

Preparation of ZT2 Medium of the Secondary Seed Tank

Components 1, total of 570 g, is dissolved by water to 30 L, and is subjected to sterilization at 121℃ for 20 min.

Components 2, total of 810 g, is dissolved by water to 5 L, and is subjected to a separate sterilization, and added when inoculating.

Components 3, total of 1350 g, is dissolved by water to 5 L, and is subjected to a separate sterilization, and added When inoculating.

In which the ZT1 culture medium comprises (g/L): diammonium hydrogen phosphate 0-25, monopotassium phosphate 0-5, disodium hydrogen phosphate 0-25, sodium chloride 0-5, $MgSO_4$ 0-0.5, $FeSO_4$ 0-1, $FeCl_3$ 0-1, $CoCl_2$ 0-1, $CuCl_2$ 0-1, $ZnCl_2$ 0-1, $Na_2MoO_4$ 0-1, $H_3BO_3$ 0-1, $MnCl_2$ 0-1, citric acid 0-25, thiamine 0-1, xylose 0-50, glycerol 0-50, glucose 0-50, sulfuric acid 0-5, and pH 6.0-7.5.

(3) Fermentation

The above secondary enlarged seed fermentation broth of 50 L is transferred to a 10 m³ fermentation tank. The starting volume is 5 m³, and the ZT2 medium is selected as the basis of the fermentation medium. The content in the tank is cultured at 33-37℃, low-ventilation, for 8-9 h; and the starting ventilation rate is 1:0.3 (feedstock: air), the dissolved oxygen is controlled to no lower than 20% during the culture by increasing rotate speed and ventilation. The pH is maintained to be 7.0 by $Ca(OH)_2$. Then, it is into non-ventilation fermentation phase, the temperature is kept at 40-45℃, the pH is maintained to be 7.0 by $Ca(OH)_2$. Glucose is replenished to the final concentration of 50 g/L (calculated based on the starting volume), the replenishment is carried out in 4 batches with a interval of 3 h. The fermentation is carried out for 20-22 h, the concentration of the remaining glucose is measured to be lower than 0.1%, and then the contents in the fermentation can be released. The above process is repeated for performing 5 batches of fermentation production. The fermentation result is shown in table 3.

TABLE 3 fermentation production result of extremely high optical pure D-lactic acid by five-batch fermentation in a 10-ton tank

| batches | Fermentation period (h) | Concentration of D-lactic acid (%, w/v) | convert ratio of substrate to product (%, w/w) | Optical purity (%, w/w) | Chemical purity (%, w/w) |
|---|---|---|---|---|---|
| 1405 | 30 | 14.5 | 86.3 | 99.96 | 97.7 |
| 1406 | 29 | 14.9 | 87.6 | 99.97 | 98.4 |
| 1407 | 32 | 15.4 | 86.1 | 99.95 | 97.8 |
| 1408 | 28 | 14.8 | 87.0 | 99.96 | 98.6 |
| 1409 | 31 | 14.8 | 86.7 | 99.98 | 97.2 |

Example 43—Fermentation of Strain to Product Extremely High Optical Pure L-lactic Acid by Five-Batch Fermentation in 10-Ton Tank According to the processes in example 42, the optimal strain obtained by the example 39 is selected as the producing strain to carry out fermentation production in a 10-ton fermentation tank for 5 batches. The fermentation result is shown in table 4.

TABLE 4 fermentation production result of extremely high optical pure L-lactic acid by five-batch fermentation in a 10-ton tank

| batches | Fermentation period (h) | Concentration of D-lactic acid (%, w/v) | convert ratio of substrate to product (%, w/w) | Optical purity (%, w/w) | Chemical purity (%, w/w) |
|---|---|---|---|---|---|
| 1410 | 34 | 18.5 | 88.7 | 99.96 | 98.7 |
| 1411 | 35 | 17.9 | 89.1 | 99.98 | 99.4 |
| 1412 | 34 | 18.4 | 88.4 | 99.96 | 98.6 |
| 1413 | 36 | 18.4 | 89.3 | 99.97 | 99.1 |
| 1414 | 35 | 17.8 | 88.5 | 99.96 | 99.2 |

Example 44—Preparation of High Optical Pure D-lactic Acid and L-lactic Acid Product Sulfuric acid with the concentration of 1%-50% is added slowly to the fermentation broth after fermentation to perform acidification. The sulfuric acid is added while stirring, wherein it is firstly added with 1%-18% of volume. The acidity is measured by $BaCl_2$ and ammonium oxalate reagent, and the addition of sulfuric acid is terminated when weak-acidity is shown. Then a reaction under stirring is conducted for 6 h, wherein the reaction end point is respectively verified by using $BaCl_2$ and an ammonium oxalate reagent.

Filtration by frame filter: the acidified fermentation broth is subjected to filter pressing through a plate-and-frame filter. After this, the resulting filter cake is washed by hot-water of 85℃ until the concentration of the lactic acid in the washing fluid is lower than 0.1%. And then, the washed filter cake is dried by compressed air, the washing liquid is merged into the clear liquid. The thallus and the solid calcium salt are used as cement or concrete materials.

Ultrafiltration: pigments, proteins, amino acids, residual thallus and the like are removed by ultrafiltration. In order to improve the efficiency of the ultrafiltration, an evaporation concentration is carried out before ultrafiltration, wherein the concentration ratio is 4:1. And the ultrafiltration is carried out on the resulting concentrated solution.

Ion exchange: the filtrate obtained after ultrafiltration is subjected to an ion-exchange.

Cation exchange: 732 cation exchange resin, which is a cation resin with a sulfonic acid group (—SO3H) on a styrene-divinyl copolymer of 7% degree of crosslinking (—SO3H) (•001×7 (732) strong-acidic styrene-based cation exchange resin); the to-be treated liquid is cooled to the room temperature before performing ion-exchange. The resin is subjected to a regeneration treatment by 5% w/v of HCl solution. Intermediate inspection: $Fe^{2+}$ does not exceed 1 ppm, and the exchange flow rate is 300 mL/min (depending on the detection result).

Anion exchange: 330 (701) weak-alkaline anion exchange resin (weakly alkaline epoxy based anion exchange resin, and is mainly used for removing $Cl^{-1}$, $SO_4^{2-}$ in water treatment, and removing inorganic acid, extracting organic acid and decolorizing, and recovering copper and silver ions); The resin is subjected to a regeneration treatment by 5% w/v of NaOH solution; the exchange flow rate is 300 mL/min (depending on the detection result); intermediate inspection: $Cl^{-1}$ does not exceed 1 ppm, $SO_4^{2-}$ does not exceed 5 ppm.

Concentration for the product: a concentration is performed until the required lactic acid concentration is reached. The product is polymer grade of D-lactic acid/L-lactic acid.

In conclusion, the present disclosure adopts the genetic engineering technology to perform dynamic regulation on the expression of the lactic acid dehydrogenase coding gene of the L- and D-lactic acid high yield recombinant strain, so that the simple fermentation process for efficiently and solely producing the D-lactic acid and L-lactic acid from glucose is realized. The method of the present disclosure, after adopting simple modification, also can be used for the construction of strain, fermentation production and the establishment and the application of novel process technology for other important microbial metabolites, but is not limited to, for example, citric acid, formic acid, acetic acid, pyruvic acid, succinic acid, malic acid, α-ketoglutaric acid, succinic acid, adipic acid, pentamethylene diamine, methacrylic acid, isoprene, itaconic acid and other organic acids and organic amines; or proline, alanine, lysine, methionine, glutamic acid, arginine and the like; thiamine, vitamin B12 and the like; or short-chain alcohol such as ethanol and propanol; or various functional sugars such as isomalto-oligosaccharide, fructo-oligosaccharide and galactooligosaccharide.

In the above examples, the nucleotide sequence of ldhA1 is a sequence shown in a sequence table<400>1, the nucleotide sequence of ldhA2 is a sequence shown in a sequence table <400>2, the nucleotide sequence of PPL1 is a sequence shown in the sequence table<400>3, the nucleotide sequence of PPL2 is a sequence shown in the sequence table<400>4, the nucleotide sequence of PPL3 is a sequence shown in the sequence table<400>5, the nucleotide sequence of PPL4 is a sequence shown in the sequence table<400>6, the nucleotide sequence of Ec-RlA1 is a sequence shown in the sequence table<400>7, the nucleotide sequence of Ec-RlA2 is a sequence shown in the sequence table<400>8, the nucleotide sequence of ThiE1p is a sequence shown in the sequence table<400>9, the nucleotide sequence of ThiE2p is a sequence shown in the sequence table<400>10, the nucleotide sequence of Dld1 is a sequence shown in the sequence table<400>11, the nucleotide sequence of Dld2 is a sequence shown in the sequence table<400>12, the nucleotide sequence of AckA-Pta1 is a sequence shown in a sequence table <400>13, the nucleotide sequence of AckA-Pta2 is a sequence shown in the sequence table<400>14, and the nucleotide sequence of Pps 1 is a sequence shown in a sequence table <400>15, and the nucleotide sequence Pps 2 of is a sequence shown in the sequence table <400>16, the nucleotide sequence of RPps 1 is a sequence shown in a sequence table <400>17, the nucleotide sequence of the RPps 2 is a sequence shown in the sequence table <400>18, the nucleotide sequence of PflB1 is a sequence shown in a sequence table <400>19, the nucleotide sequence of PflB2 is a sequence shown in the sequence table <400>20, the nucleotide sequence of PoxB1 is a sequence shown in the sequence table <400>21, the nucleotide sequence of PoxB2 is a sequence shown in the sequence table <400>22, the nucleotide sequence of FrdA1 is a sequence shown in a sequence table <400>23, the nucleotide sequence of FrdA2 is a sequence shown in a sequence table <400=24, the AdhE1 nucleotide sequence is a sequence shown in a sequence table <400>25, the nucleotide sequence of AdhE2 is a sequence shown in the sequence table <400>26, the nucleotide sequence of ldhA3 is a sequence shown in the sequence table <400>27, the nucleotide sequence of ldhA4 is a sequence shown in a sequence table <400>28, the nucleotide sequence of ldhA5 is a sequence shown in the sequence table <400>29, the nucleotide sequence of ldhA6 is a sequence shown in the sequence table <400>30, the nucleotide sequence of RldhA1 is a sequence shown in a sequence table <400>31, the nucleotide sequence of RldhA2 is a sequence shown in the sequence table <400>32, the nucleotide sequence of BcoaLDH1 is a sequence shown in a sequence table <400>33, the nucleotide sequence of BcoaLDH4 is a sequence shown in a sequence table <400>34, the nucleotide sequence of LldD1 is a sequence shown in the sequence table <400>35, the nucleotide sequence of LldD2 is a sequence shown in a sequence table <400>36, the nucleotide sequence of LcaLDH1 is a sequence shown in a sequence table <400>37, the nucleotide sequence of LcaLDH4 is a sequence shown in the sequence table <400>38, the nucleotide sequence of StrbLDH1 is a sequence shown in the sequence table <400>39, the nucleotide sequence of the StrbLDH2 is a sequence shown in the sequence table <400>40. The specific information is as follows:

The information of SEQ ID No. 1:
(i) sequence features:
(A) length: 27 bp
(B) type: nucleic acid
(C) chain property: single chain
(D) topological structure: linear
(ii) molecular type: oligonucleotide
(iii) description to the sequence: SEQ ID No. 1
ldhA1:    TCCGGTACCCAGCCCGAGCGTCATCAG; KpnI The information of SEQ ID No. 2:
(i) sequence features:
(A) length: 25 bp
(B) type: nucleic acid
(C) chain property: single chain
(D) topological structure: linear
(ii) molecular type: oligonucleotide
(iii) description to the sequence: SEQ ID No. 2
ldhA2: GTCAAGGTCGACGTTATTGAAACCG;

The information of SEQ ID No. 3:
(i) sequence features:
(A) length: 28 bp
(B) type: nucleic acid
(C) chain property: single chain
(D) topological structure: linear
(ii) molecular type: oligonucleotide
(iii) description to the sequence: SEQ ID No. 3
PPL1: AGCTTGGCTGCAGGTGATGATTATCAGC;

The information of SEQ ID No. 4:
(i) sequence features:
(A) length: 24 bp
(B) type: nucleic acid
(C) chain property: single chain
(D) topological structure: linear
(ii) molecular type: oligonucleotide
(iii) description to the sequence: SEQ ID No. 4
PPL2: ATCGCCGGCAATTCGTAATCATGG; EcoRI The information of SEQ ID No. 5:
(i) sequence features:
(A) length: 30 bp
(B) type: nucleic acid
(C) chain property: single chain
(D) topological structure: linear
(ii) molecular type: oligonucleotide
(iii) description to the sequence: SEQ ID No. 5
PPL3: TAAGATATCCCATGATTACGAATTGCCGGC; EcoRV The information of SEQ ID No. 6:
(i) sequence features:
(A) length: 37 bp
(B) type: nucleic acid
(C) chain property: single chain
(D) topological structure: linear
(ii) molecular type: oligonucleotide
(iii) description to the sequence: SEQ ID No. 6
PPL4:    TAAGAATTCAGTTAACCTCCTTAGGATC-CCAATGCTT EcoRI The information of SEQ ID No. 7:
(i) sequence features:
(A) length: 39 bp
(B) type: nucleic acid
(C) chain property: single chain
(D) topological structure: linear
(ii) molecular type: oligonucleotide
(iii) description to the sequence: SEQ ID No. 7
Ec-RlA1:    TAAGAATTCATGAAACTCGCCGTT-TATAGCACAAAACAG; EcoRI The information of SEQ ID No. 8:
(i) sequence features:
(A) length: 30 bp
(B) type: nucleic acid
(C) chain property: single chain
(D) topological structure: linear
(ii) molecular type: oligonucleotide
(iii) description to the sequence: SEQ ID No. 8
Ec-RlA2: AAGACTTTCTCCAGTGATGTTGAATCACAT;

The information of SEQ ID No. 9:
(i) sequence features:
(A) length: 29 bp
(B) type: nucleic acid
(C) chain property: single chain
(D) topological structure: linear
(ii) molecular type: oligonucleotide
(iii) description to the sequence: SEQ ID No. 9
ThiE1p: AGAGAATTCATTCATCGCCAACTCCTGCA The information of SEQ ID No. 10:
(i) sequence features:
(A) length: 32 bp
(B) type: nucleic acid
(C) chain property: single chain
(D) topological structure: linear
(ii) molecular type: oligonucleotide
(iii) description to the sequence: SEQ No. 10
ThiE2p: AGAGAATTCGGTGGACAGCGTACAGTGGATCG;

The information of SEQ ID No. 11:
(i) sequence features:
(A) length: 26 bp
(B) type: nucleic acid
(C) chain property: single chain
(D) topological structure: linear
(ii) molecular type: oligonucleotide
(iii) description to the sequence: SEQ ID No. 11
Dld1: AGTACGTCTTGATACCTTCGAAGCGG;

The information of SEQ ID No. 12:
(i) sequence features:
(A) length: 23 bp
(B) type: nucleic acid
(C) chain property: single chain
(D) topological structure: linear
(ii) molecular type: oligonucleotide
(iii) description to the sequence: SEQ ID No. 12
Dld2: GGATTCATGCTGTTGGTCGGATC;

The information of SEQ ID No. 13:
(i) sequence features:
(A) length: 23 bp
(B) type: nucleic acid
(C) chain property: single chain
(D) topological structure: linear
(ii) molecular type: oligonucleotide
(iii) description to the sequence: SEQ ID No. 13
AckA-Pta1: TGAACATCATCACCTGCCACCTG;

The information of SEQ ID No. 14:
(i) sequence features:
(A) length: 19 bp
(B) type: nucleic acid
(C) chain property: single chain
(D) topological structure: linear
(ii) molecular type: oligonucleotide
(iii) description to the sequence: SEQ ID No. 14
AckA-Pta2: CAGCGCAAAGCTGCGGATG The information of SEQ No. 15:
(i) sequence features:
(A) length: 25 bp
(B) type: nucleic acid
(C) chain property: single chain
(D) topological structure: linear
(ii) molecular type: oligonucleotide
(iii) description to the sequence: SEQ ID No. 15
Pps1: CGGCATGAATGATGTAGACAGGGTT The information of SEQ ID No. 16:
(i) sequence features:
(A) length: 23 bp
(B) type: nucleic acid
(C) chain property: single chain
(D) topological structure: linear
(ii) molecular type: oligonucleotide
(iii) description to the sequence: SEQ ID No. 16
Pps2: TAACCAGGTTTGCACCACGGTGT The information of SEQ ID No. 17:
(i) sequence features:
(A) length: 21 bp
(B) type: nucleic acid
(C) chain property: single chain
(D) topological structure: linear
(ii) molecular type: oligonucleotide
(iii) description to the sequence: SEQ ID No. 17
RPps1: TGTGGCGAAACCATTCGGAAC The information of SEQ ID No. 18:
(i) sequence features:
(A) length: 22 bp
(B) type: nucleic acid
(C) chain property: single chain
(D) topological structure: linear
(ii) molecular type: oligonucleotide
(iii) description to the sequence: SEQ ID No. 18
RPps2: GTCCGACCACGAAGACTTTGCC The information of SEQ ID No. 19:
(i) sequence features:
(A) length: 23 bp
(B) type: nucleic acid
(C) chain property: single chain
(D) topological structure: linear
(ii) molecular type: oligonucleotide
(iii) description to the sequence: SEQ ID No. 19
PflB1: TTCAGACTTCGGACCAACCTGCA The information of SEQ ID No. 20:
(i) sequence features:
(A) length: 20 bp
(B) type: nucleic acid
(C) chain property: single chain
(D) topological structure: linear
(ii) molecular type: oligonucleotide
(iii) description to the sequence: SEQ ID No. 20
PflB2: CCGCGAACTGGATCCGATGA;

The information of SEQ ID No. 21:
(i) sequence features:
(A) length: 24 bp
(B) type: nucleic acid
(C) chain property: single chain
(D) topological structure: linear
(ii) molecular type: oligonucleotide
(iii) description to the sequence: SEQ ID No. 21
PoxB1: CAAACGGTTGCAGCTTATATCGCC The information of SEQ ID No 22:
(i) sequence features:
(A) length: 24 bp
(B) type: nucleic acid (C) chain property: single chain
(D) topological structure: linear
(ii) molecular type: oligonucleotide
(iii) description to the sequence: SEQ ID No. 22
PoxB2: TGCGGTGGAATGGCTAACTCTTCT
The information of SEQ ID No. 23:
(i) sequence features:
(A) length: 23 bp
(B) type: nucleic acid
(C) chain property: single chain
(D) topological structure: linear
(ii) molecular type: oligonucleotide
(iii) description to the sequence: SEQ. ID No. 23
FrdA1: CTTTCAAGCCGATCTTGCCATTG
The information of SEQ ID No. 24:
(i) sequence features:
(A) length: 24 bp
(B) type: nucleic acid
(C) chain property: single chain
(D) topological structure: linear
(ii) molecular type: oligonucleotide
(iii) description to the sequence: SEQ ID No. 24
FrdA2: ACTCTTTACGTGCCATTGCGGAGT
The information of SEQ ID No. 25:
(i) sequence features:
(A) length: 24 bp
(B) type: nucleic acid
(C) chain property; single chain
(D) topological structure: linear
(ii) molecular type: oligonucleotide
(iii) description to the sequence: SEQ ID No. 25
AdhE1: ATCTGATCGGCTGGATCGATCAAC
The information of SEQ No. 26:
(i) sequence features:
(A) length: 22 bp
(B) type: nucleic acid
(C) chain property: single chain
(D) topological structure: linear
(ii) molecular type: oligonucleotide
(iii) description to the sequence: SEQ ID No. 26
AdhE2: GAACCAGGTTGGCGTCGACAAT
The information of SEQ ID No. 27:
(i) sequence features:
(A) length: 35 bp
(B) type: nucleic acid
(C) chain property: single chain
(D) topological structure: linear
(ii) molecular type: oligonucleotide
(iii) description to the sequence: SEQ ID No. 27
ldhA3: TAAGAATTCTTATGAAACTCGCCGTT-TATAGCACA EcoRI
The information of SEQ ID No. 28:
(i) sequence features:
(A) length: 38 bp
(B) type: nucleic acid
(C) chain property: single chain
(D) topological structure: linear
(ii) molecular type: oligonucleotide
(iii) description to the sequence: SEQ ID No. 28
ldhA4: CTTGAATTCAAGCTTGCTGCCGGAAAT-CATCATTTTTT EcoRI, HindIII
The information of SEQ ID No. 29:
(i) sequence features:
(A) length: 21 bp
(B) type: nucleic acid
(C) chain property: single chain
(D) topological structure: linear
(ii) molecular type: oligonucleotide
(iii) description to the sequence: SEQ ID No. 29
ldhA5: GGGCAGCCCGAGCGTCATCAG
The information of SEQ ID No. 30:
(i) sequence features:
(A) length: 23 bp
(B) type: nucleic acid
(C) chain property: single chain
(D) topological structure: linear
(ii) molecular type: oligonucleotide
(iii) description to the sequence: SEQ No. 30
ldhA6: GCTGCCGGAAATCATCATTTTTT
The information of SEQ ID No. 31:
(i) sequence features:
(A) length: 30 bp
(B) type: nucleic acid
(C) chain property: single chain
(D) topological structure: linear
(ii) molecular type: oligonucleotide
(iii) description to the sequence: SEQ ID No. 31
RldhA1; GGAAGATCTTCCGC-GAGTTTCATAAGACTT BglII
The information of SEQ ID No. 32:
(i) sequence features;
(A) length: 24 bp
(B) type: nucleic acid
(C) chain property: single chain
(D) topological structure: linear
(ii) molecular type: oligonucleotide
(iii) description to the sequence: SEQ ID No. 32
RldhA2: CGGAATTCCGAACGAACTGGTTTA EcoR
The information of SEQ ID No. 33:
(i) sequence features:
(A) length: 33 bp
(B) type: nucleic acid
(C) chain property: single chain
(D) topological structure: linear
(ii) molecular type: oligonucleotide
(iii) description to the sequence: SEQ ID No. 33
BcoaLDH1 CCGGATCCAATCAGGGTGTTGCA-GAAGAGCTTG BamHI
The information of SEQ ID No. 34:
(i) sequence features;
(A) length: 34 bp
(B) type: nucleic acid
(C) chain property: single chain
(D) topological structure: linear
(ii) molecular type: oligonucleotide
(iii) description to the sequence: SEQ ID No. 34
BcoaLDH4 GCGGAATTCTTACAATACAGGTGC-CATCGTTTCT EcoRI
The information of SEQ ID No. 35:
(i) sequence features:
(A) length: 28 bp
(B) type: nucleic acid
(C) chain property: single chain
(D) topological structure: linear
(ii) molecular type: oligonucleotide
(iii) description to the sequence: SEQ ID No. 35
LldD1 GGCCCGGGCATGATTATTTCCGCAGCCA SmaI
The information of SEQ ID No. 36:
(i) sequence features:
(A) length: 30 bp
(B) type: nucleic acid (C) chain property: single chain
(D) topological structure: linear
(ii) molecular type: oligonucleotide
(iii) description to the sequence: SEQ ID No. 36
LldD2: GGCCCGGGCAGGCAACTCTTTACCCA-GCCC SmaI The information of SEQ ID No. 37:
(i) sequence features:
(A) length: 30 bp
(B) type: nucleic acid
(C) chain property: single chain
(D) topological structure: linear
(ii) molecular type: oligonucleotide
(iii) description to the sequence: SEQ ID No. 37
LcaLDH1 CGCGGATCCAGTATTACGGATAAGGAT-CAC BamHI The information of SEQ ID No. 38:
(i) sequence features:
(A) length: 25 bp
(B) type: nucleic acid
(C) chain property: single chain
(D) topological structure: linear
(ii) molecular type: oligonucleotide
(iii) description to the sequence: SEQ ID No. 38
LcaLDH4 CGCCTGCAGTCCTGTTCTTCGTTTG PstI The information of SEQ ID No. 39:
(i) sequence features:
(A) length: 28 bp
(B) type: nucleic acid
(C) chain property: single chain
(D) topological structure: linear
(ii) molecular type: oligonucleotide
(iii) description to the sequence: SEQ ID No. 39
StrbLDH1 CGCGGATCCACTAAACAACA-CAAAAAAG BamHI The information of SEQ ID No. 40:
(i) sequence features:
(A) length: 28 bp
(B) type: nucleic acid
(C) chain property: single chain
(D) topological structure: linear
(ii) molecular type: oligonucleotide
(iii) description to the sequence: SEQ ID No. 40
StrbLDH2 CCGGAATTCTACAGGGATTGTTGC-CGCA EcoRI The above is the detailed description of polymer grade lactic acid monomer production bacteria and construction methods thereof and technology for manufacturing lactic acid with reference to the above examples. The description is intended to be illustrative but not restrictive, and several examples can be listed according to the defined range. Therefore, any changes and modifications departing from the general concept of the present invention shall fall within the protection scope of the present invention.

What is claimed is:

1. A polymer grade lactic acid monomer producing strain for producing extremely high optically pure L-lactic acid by fermentation, wherein, the deposit number of the strain is CGMCC No. 11060, an extremely high optical purity means that the optical purity of L-lactic produced by the strain≥99.9%.

* * * * *